(12) United States Patent
Luo et al.

(10) Patent No.: US 7,709,198 B2
(45) Date of Patent: May 4, 2010

(54) MULTIPLEX DETECTION OF NUCLEIC ACIDS

(75) Inventors: Yuling Luo, San Ramon, CA (US); Yunqing Ma, Cupertino, CA (US); Cung-Tuong Nguyen, Milpitas, CA (US)

(73) Assignee: Advanced Cell Diagnostics, Inc., Haywood, CA (US)

( * ) Notice: Subject to any disclaimer, the term of this patent is extended or adjusted under 35 U.S.C. 154(b) by 0 days.

(21) Appl. No.: 11/471,025

(22) Filed: Jun. 19, 2006

(65) Prior Publication Data
US 2007/0015188 A1 Jan. 18, 2007

Related U.S. Application Data

(60) Provisional application No. 60/691,834, filed on Jun. 20, 2005.

(51) Int. Cl.
C12Q 1/68 (2006.01)
C12P 19/34 (2006.01)
C07H 21/02 (2006.01)
C07H 21/04 (2006.01)

(52) U.S. Cl. .............. 435/6; 435/91.1; 435/287.2; 536/23.1; 536/24.3

(58) Field of Classification Search .............. 435/6, 435/91.1, 287.2; 536/23.1, 24.3
See application file for complete search history.

(56) References Cited

U.S. PATENT DOCUMENTS

| | | | |
|---|---|---|---|
| 4,868,105 A | 9/1989 | Urdea et al. |
| 5,093,232 A | 3/1992 | Urdea et al. |
| 5,122,599 A | 6/1992 | Barnett et al. |
| 5,124,246 A | 6/1992 | Urdea et al. |
| 5,185,244 A | 2/1993 | Wallace |
| 5,198,357 A | 3/1993 | Holmovist et al. |
| 5,334,499 A | 8/1994 | Burdick et al. |
| 5,374,524 A | 12/1994 | Miller |
| 5,393,672 A | 2/1995 | Ness et al. |
| 5,543,305 A | 8/1996 | Cummins et al. |
| 5,633,134 A | 5/1997 | Shuber |
| 5,635,352 A * | 6/1997 | Urdea et al. .............. 435/6 |
| 5,681,697 A | 10/1997 | Urdea et al. |
| 5,681,702 A | 10/1997 | Collins et al. |
| 5,747,244 A | 5/1998 | Sheridan et al. |
| 5,780,227 A | 7/1998 | Sheridan et al. |
| 5,804,684 A | 9/1998 | Su |
| 5,849,481 A | 12/1998 | Urdea et al. |
| 5,888,778 A | 3/1999 | Shuber |
| 5,945,515 A | 8/1999 | Chomczynski |
| 6,007,994 A | 12/1999 | Ward et al. |
| 6,221,589 B1 | 4/2001 | Lane et al. |
| 6,232,462 B1 | 5/2001 | Collins et al. |
| 6,268,147 B1 | 7/2001 | Beattie et al. |
| 6,306,643 B1 | 10/2001 | Gentalen et al. |
| 6,352,827 B1 | 3/2002 | Lin et al. |
| 6,418,382 B2 | 7/2002 | Rothberg et al. |
| 6,428,957 B1 | 8/2002 | Delenstarr |
| 6,610,475 B1 | 8/2003 | Kacian et al. |
| 6,670,464 B1 | 12/2003 | Shimkets et al. |
| 6,673,914 B1 | 1/2004 | Hoon |
| 6,852,490 B2 | 2/2005 | Gentalen et al. |
| 7,033,758 B2 | 4/2006 | Kenny et al. |
| 2002/0034753 A1* | 3/2002 | Yang et al. .............. 435/6 |
| 2002/0034754 A1 | 3/2002 | Reed et al. |
| 2002/0106644 A1 | 8/2002 | Rosenow |
| 2002/0172953 A1 | 11/2002 | Mirkin et al. |
| 2002/0187470 A1 | 12/2002 | Casey et al. |
| 2003/0165935 A1 | 9/2003 | Vann et al. |
| 2003/0211489 A1 | 11/2003 | Shen et al. |
| 2004/0023248 A1 | 2/2004 | O'Malley |
| 2004/0072231 A1 | 4/2004 | Mirkin et al. |
| 2004/0076954 A1 | 4/2004 | Caldwell et al. |
| 2004/0086930 A1 | 5/2004 | Tereba et al. |
| 2004/0115686 A1 | 6/2004 | Dolginow et al. |
| 2005/0009063 A1 | 1/2005 | Xia et al. |
| 2005/0037397 A1 | 2/2005 | Mirkin et al. |
| 2005/0170370 A1 | 8/2005 | Rabbani et al. |
| 2005/0282220 A1 | 12/2005 | Prober et al. |

(Continued)

FOREIGN PATENT DOCUMENTS

EP      1 428 892 A      6/2004

(Continued)

OTHER PUBLICATIONS

Van Cleve et al, Direct quantitation of HIV by flow cytometry using branched DNA signal amplification, 1998, Molecular and Celluar Probes, 12, 243-247.*

(Continued)

*Primary Examiner*—Stephen Kapushoc
*Assistant Examiner*—Narayan K Bhat
(74) *Attorney, Agent, or Firm*—Quine Intellectual Property Law Group, P.C.; Monica Elrod-Erickson

(57) ABSTRACT

Methods of detecting nucleic acids, including methods of detecting two or more nucleic acids in multiplex branched-chain DNA assays, are provided. Nucleic acids captured on a solid support are detected, for example, through cooperative hybridization events that result in specific association of a label with the nucleic acids. Compositions, kits, and systems related to the methods are also described.

45 Claims, 7 Drawing Sheets

U.S. PATENT DOCUMENTS

| | | |
|---|---|---|
| 2006/0172284 A1 | 8/2006 | Zheng et al. |
| 2006/0263769 A1 | 11/2006 | Luo et al. |
| 2006/0286583 A1 | 12/2006 | Luo et al. |
| 2007/0161015 A1 | 7/2007 | Zheng et al. |
| 2007/0161020 A1 | 7/2007 | Luo et al. |
| 2008/0038725 A1 | 2/2008 | Luo et al. |
| 2008/0050746 A1 | 2/2008 | McMaster et al. |
| 2008/0176242 A1 | 7/2008 | McMaster et al. |
| 2009/0081688 A1 | 3/2009 | Luo et al. |
| 2009/0170060 A1 | 7/2009 | Kermekchiev et al. |

FOREIGN PATENT DOCUMENTS

| | | |
|---|---|---|
| WO | WO 94/00598 A1 | 1/1994 |
| WO | WO 01/94632 A2 | 12/2001 |
| WO | WO 2004/020654 A2 | 3/2004 |
| WO | WO 2006/124771 A2 | 11/2006 |
| WO | WO 2007/001986 A2 | 1/2007 |

OTHER PUBLICATIONS

Malygin et al, Hybridization of two oligodeoxynucleotides to both strands of an RNA hairpin structure increases the efficiency of RNA-DNA duplex formation, 1996, FEBS Letters, 392, 114-116.*

Bushnell et al. (1999) "ProbeDesigner: for the design of probe sets for branched DNA (bDNA) signal amplification assays," *Bioinformatics*, 15(5):348-355.

Collins et al. (1997) "A branched DNA signal amplification assay for quantification of nucleic acid targets below 100 molecules/ml," *Nucleic Acids Research*, 25(15):2979-2984.

Collins et al. (1998) "Branched DNA (bDNA) technology for direct quantification of nucleic acids: design and performance," in *Gene Quantification*, F. Ferre, ed.

Flagella et al. (2006) "A multiplex branched DNA assay for parallel quantitative gene expression profiling," *Anal. Biochem.*, 352(1):50-60.

Fulton et al. (1997) "Advanced multiplexed analysis with the FlowMetrix system," *Clin Chem.*, 43:1749-1756.

Gentalen & Chee. (1999) "A novel method for determining linkage between DNA sequences: hybridization to paired probe arrays," *Nucleic Acids Research*, 27(6):1485-1491.

Iannone (2000) "Multiplexed single nucleotide polymorphism genotyping by oligonucleotide ligation and flow cytometry," *Cytometry*, 39(2):131-140.

Player et al. (2001) "Single-copy gene detection using branched DNA (bDNA) in situ hybridization" J Histochem Cytochem 49:603-611.

Wang et al. (1997) "Regulation of insulin preRNA splicing by glucose," *Proc. Nat. Acad. Sci. USA*, 94(9):4360-4365.

Wilber & Urdea (1998) "Quantification of HCV RNA in clinical specimens by branched DNA (bDNA) technology," *Methods in Molecular Medicine: Hepatitis C* 19:71-78.

Yang et al. (2001) "BADGE, Beads Array for the Detection of Gene Expression, a high-throughput diagnostic bioassay," *Genome Res.*, 11(11):1888-1898.

Dimitrov and Zuker (2004) "Prediction of hybridization and melting for double-stranded nucleic acids," *Biophysical Journal*, 87(1):215-226.

Al-Soud et al. (1998) "A sample preparation method which facilitates detection of bacteria in blood cultures by the polymerase chain reaction," *J. Microbiol. Meth.*, 32:217-224.

Application Note from Amersham Biosciences, "Whole genome amplification from crude blood lysates," 2003 (4 pages).

Application Note from Applied Biosystems, "Total RNA purification from whole blood," 2002 (6 pages).

Bach et al. (1999) "Magnetic capture-hybridization method for purification and probing of mRNA for neutral protease of *Bacillus cereus*," *J Microbiological Methods*, 37:187-192.

Balnaves et al. (1991) "Direct PCR from CVS and blood lysates for detection of cystic fibrosis and Duchenne muscular dystrophy deletions," *Nucl. Acids. Res.*, 19(5):1155.

Borucki et al. (2005) "Suspension microarray with dendrimer signal amplification allows direct and high-throughput subtyping of *Listeria monocytogenes* from genomic DNA," *J. Clin. Microbiol.*, 3255-3259.

De Vries et al. (2001) "PCR on cell lysates obtained from whole blood circumvents DNA isolation," *Clin. Chem.* 47(9):1701-1702.

Higuchi (1989) "DNA from whole blood for PCR," *Amplifications*, 2:1-3 (One page from The Jackson Libaray, http://www.jax.org.imr.whole_blood.html).

Kenny et al. (2002) "Detection of viral infection and gene expression in clinical tissue specimens using branched DNA (bDNA) in situ hybridization," 50(9):1219-1227.

Kern et al. (1996) "An enhanced-sensitivity branched-DNA assay for quantification of human immunodeficiency virus type 1 RNA in plasma," *J. Clin. Microbiol.*, 34(12):3196-3202.

Lewin & Stewart-Haynes (1992) "A simple method for DNA extraction from leukocytes for use in PCR," *BioTechniques*, 13(4):522-524.

Lo et al. (2000) "Fetal DNA in maternal plasma: biology and diagnostic applications," *Clinical Chemistry*, 46(12):1903-1906.

Mercier et al. (1990) "Direct PCR from whole blood, without DNA extraction," *Nucl. Acids. Res.*, 18(19):5908.

Narayanan (1992) "Overview of principles and current uses of DNA probes in clinical and laboratory medicine," *Ann. Clin. Lab. Sci.*, 22(6):353-376.

Nordvag et al. (1992) "Direct PCR of washed blood cells," *BioTechniques*, 12(4):490-493.

Schweitzer & Kingsmore (2001) "Combining nucleic acid amplification and detection," *Curr. Op Biotechnol.*, 12(1):21-27.

Shah et al. (1994) "Novel, ultrasensitive, Q-beta, replicase-amplified hybridization assay for detection of *Chlamydia trachomatis*," *J. Clin. Microbiol.*, 32(11):2718-2724.

Shah et al. (1995) "Detection of *Mycobacterium tuberculosis* directly from spiked human sputum by Q-beta replicase-amplifiied assay," *J. Clin. Microbiol.*, 33(2):322-328.

Shah et al. (2003) "Ultra-sensitive and specific detections of porcine endogenous retrovirus (PERV) using a sequence-capture real-time PCR approach," *J. Virol.Meth.*, 109:209-216.

Stone et al. (1996) "Detection of rRNA from four respiratory pathogens using an automated Qβ replicase assay," *Mol. Cell. Probes*, 10:359-370.

Ugozzoli et al. (1992) "Detection of specific alleles by using allele-specific primer extension followed by capture on solid support," *GATA*, 9(4):107-112.

Zhang et al. (2005) "Small interfering RNA and gene expression analysis using a multiplex branched DNA assay without RNA purification," *J. Biomolecular Screening*, 10(6):549-556.

Zolg et al. (1988) "High salt lysates: a simple method to stores blood samples without refrigeration for subsequent use with DNA probes," *Am. J. Trop. Med. Hyg.*, 39(1):33-40.

Bortolin et al. (2004) "Analytical validation of the tag-it high-throughput microsphere-based universal array genotyping platform: application to the multiplex detection of a panel of thrombophilia-associated single-nucleotide polymorphisms," *Clin. Chem.*, 50(11):2028-2036.

Burris et al. (1999) "A novel method for analysis of nuclear receptor function at natural promoters: peroxisome proliferator-activated receptor γ agonist actions on aP2 gene expression detected using branched DNA messenger RNA quantitation," *Molecular Endocrinology*, 13(3):410-417.

Hartley and Klaassen (2000) "Detection of chemical-induced differential expression of rat hepatic cytochrome P450 mRNA transcripts using branched DNA signal amplification technology," *Drug Metabolism and Disposition*, 28(5):608-616.

Nolte (1998) "Branched DNA signal amplification for direct quantitation of nucleic acid sequences in clinical specimens," *Advances in Clinical Chemistry*, 33(1):201-235.

Shen et al. (1998) "Quantification of cytokine mRNA in peripheral blood mononuclear cells using branched DNA (bDNA) technology," *J. Immunol. Meth.*, 215(1-2):123-134.

Tsai et al. (2003) "Nucleic acid capture assay, a new method for direct quantitation of nucleic acids," *Nucleic Acids Research*, 31(6):e25.

Wilson et al. (2005) "A multiplexed PCR-coupled liquid bead array for the simultaneous detection of four biothreat agents," *Mol.Cell. Probes*, 19(2):137-144.

* cited by examiner

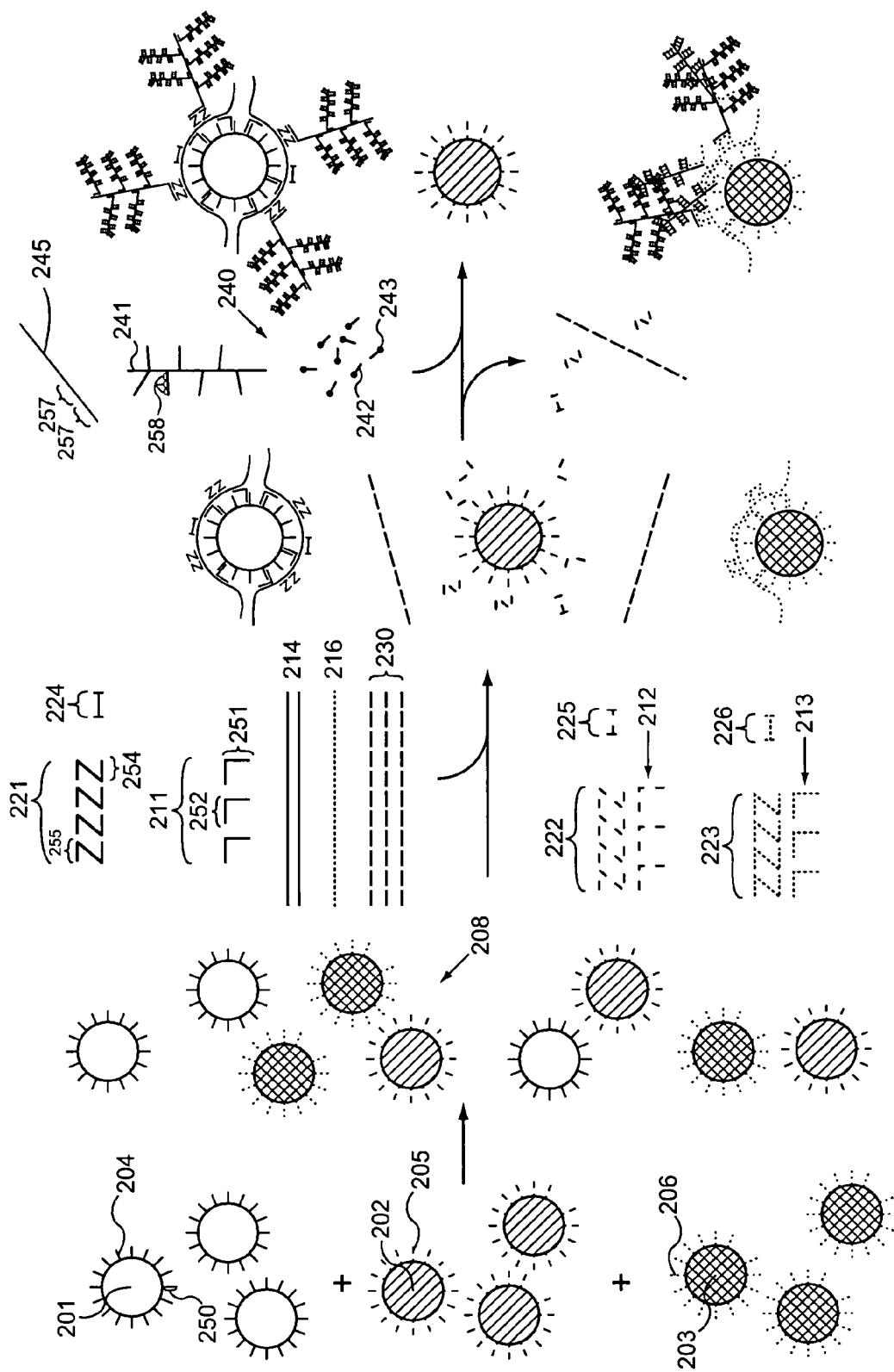

MULTIPLEX DETECTION OF NUCLEIC ACIDS

CROSS-REFERENCE TO RELATED APPLICATIONS

This application is a non-provisional utility patent application claiming priority to and benefit of the following prior provisional patent application: U.S. Ser. No. 60/691,834, filed Jun. 20, 2005, entitled "Method of Detecting and Enumerating Rare Cells from Large Heterogeneous Cell Populations" by Luo and Chen, which is incorporated herein by reference in its entirety for all purposes.

FIELD OF THE INVENTION

The present invention is in the field of nucleic acid detection. The invention includes methods for detecting nucleic acids, including methods for detecting the presence of two or more nucleic acids simultaneously in a single sample. The invention also includes compositions and kits related to the methods.

BACKGROUND OF THE INVENTION

Global gene expression profiling and other technologies have identified a large number of genes whose expression is altered, e.g., in diseased tissues or in tissues and cells treated with pharmaceutical agents (Lockhart and Winzeler (2000) "Genomics, gene expression and DNA arrays" Nature 405: 827-36 and Gunther et al. (2003) "Prediction of clinical drug efficacy by classification of drug-induced genomic expression profiles in vitro" Proc Natl Acad Sci USA 100:9608-13). Such genes are being increasingly used as biomarkers in disease diagnosis, staging, and prognosis (Golub et al. (1999) "Molecular classification of cancer: class discovery and class prediction by gene expression monitoring" Science 286:531-7); target identification, validation and pathway analysis (Roberts et al. (2000) "Signaling and circuitry of multiple MAPK pathways revealed by a matrix of global gene expression profiles" Science 287:873-80); drug screening (Hamadeh et al. (2002) "Prediction of compound signature using high density gene expression profiling" Toxicol Sci 67:232-40); and studies of drug efficacy, structure-activity relationship, toxicity, and drug-target interactions (Gerhold et al. (2001) "Monitoring expression of genes involved in drug metabolism and toxicology using DNA microarrays" Physiol Genomics 5:161-70 and Thomas et al. (2001) "Identification of toxicologically predictive gene sets using cDNA microarrays" Mol Pharmacol 60:1189-94). As biomarkers are identified, their involvement in disease management and drug development will need to be evaluated in higher throughput and broader populations of samples. Simpler and more flexible expression profiling technology that allows the expression analysis of multiple genes with higher data quality and higher throughput is therefore needed.

Levels of RNA expression have traditionally been measured using Northern blot and nuclease protection assays. However, these approaches are time-consuming and have limited sensitivity, and the data generated are more qualitative than quantitative in nature. Greater sensitivity and quantification are possible with reverse transcription polymerase chain reaction (RT-PCR) based methods, such as quantitative real-time RT-PCR, but these approaches have low multiplex capabilities (Bustin (2002) "Quantification of mRNA using real-time reverse transcription PCR (RT-PCR): trends and problems" J Mol Endocrinol 29:23-39 and Bustin and Nolan (2004) "Pitfalls of quantitative real-time reverse-transcription polymerase chain reaction" J Biomol Tech. 15:155-66). Microarray technology has been widely used in discovery research, but its moderate sensitivity and its relatively long experimental procedure have limited its use in high throughput expression profiling applications (Epstein and Butow (2000) "Microarray technology—enhanced versatility, persistent challenge" Curr Opin Biotechnol. 11:36-41).

Most of the current methods of mRNA quantification require RNA isolation, reverse transcription, and target amplification, each of which introduces variability that leads to low overall assay precision. Recently, a multiplex screening assay for mRNA quantification combining nuclease protection with luminescent array detection was reported (Martel et al. (2002) "Multiplexed screening assay for mRNA combining nuclease protection with luminescent array detection" Assay Drug Dev Technol. 1:61-71). Although this assay has the advantage of measuring mRNA transcripts directly from cell lysates, limited assay sensitivity and reproducibility were reported. Another multiplex mRNA assay without the need for RNA isolation was also reported (Tian et al. (2004) "Multiplex mRNA assay using electrophoretic tags for high-throughput gene expression analysis" Nucleic Acids Res. 32:e126). This assay couples the primary Invader® mRNA assay with small fluorescent molecule eTags that can be distinguished by capillary electrophoresis through distinct charge-to-mass ratios of eTags. However, this assay requires the use of a specially designed and synthesized set of eTagged signal probes, complicated capillary electrophoresis equipment, and a special data analysis package.

Among other aspects, the present invention provides methods that overcome the above noted limitations and permit rapid, simple, and sensitive detection of multiple mRNAs (and/or other nucleic acids) simultaneously. A complete understanding of the invention will be obtained upon review of the following.

SUMMARY OF THE INVENTION

In one aspect, the present invention provides methods for detecting nucleic acids of interest. The nucleic acids are captured to a solid support and then detected. Compositions, kits, and systems related to the methods are also provided.

A first general class of embodiments includes methods of detecting two or more nucleic acids of interest. In the methods, a sample comprising or suspected of comprising the nucleic acids of interest, two or more subsets of m label extenders, wherein m is at least two, and a label probe system are provided. Each subset of m label extenders is capable of hybridizing to one of the nucleic acids of interest. The label probe system comprises a label, and a component of the label probe system is capable of hybridizing simultaneously to at least two of the m label extenders in a subset.

Those nucleic acids of interest present in the sample are captured on a solid support. Each nucleic acid of interest captured on the solid support is hybridized to its corresponding subset of m label extenders, and the label probe system is hybridized to the m label extenders. The presence or absence of the label on the solid support is then detected. Since the label is associated with the nucleic acid(s) of interest via hybridization of the label extenders and label probe system, the presence or absence of the label on the solid support is correlated with the presence or absence of the nucleic acid(s) of interest on the solid support and thus in the original sample.

In one class of embodiments, a pooled population of particles which constitute the solid support is provided. The population comprises two or more subsets of particles, and a plurality of the particles in each subset is distinguishable from a plurality of the particles in every other subset. The particles in each subset have associated therewith a different capture probe. Two or more subsets of n capture extenders, wherein n is at least two, are also provided. Each subset of n capture extenders is capable of hybridizing to one of the nucleic acids of interest, and the capture extenders in each subset are capable of hybridizing to one of the capture probes, thereby associating each subset of n capture extenders with a selected subset of the particles. Each of the nucleic acids of interest present in the sample is hybridized to its corresponding subset of n capture extenders and the subset of n capture extenders is hybridized to its corresponding capture probe, thereby capturing the nucleic acid on the subset of particles with which the capture extenders are associated.

Typically, in this class of embodiments, at least a portion of the particles from each subset are identified and the presence or absence of the label on those particles is detected. Since a correlation exists between a particular subset of particles and a particular nucleic acid of interest, which subsets of particles have the label present indicates which of the nucleic acids of interest were present in the sample.

In another class of embodiments, the solid support comprises two or more capture probes, wherein each capture probe is provided at a selected position on the solid support. Two or more subsets of n capture extenders, wherein n is at least two, are provided. Each subset of n capture extenders is capable of hybridizing to one of the nucleic acids of interest, and the capture extenders in each subset are capable of hybridizing to one of the capture probes, thereby associating each subset of n capture extenders with a selected position on the solid support. Each of the nucleic acids of interest present in the sample is hybridized to its corresponding subset of n capture extenders and the subset of n capture extenders is hybridized to its corresponding capture probe, thereby capturing the nucleic acid on the solid support at the selected position with which the capture extenders are associated.

Typically, in this class of embodiments, the presence or absence of the label at the selected positions on the solid support is detected. Since a correlation exists between a particular position on the support and a particular nucleic acid of interest, which positions have a label present indicates which of the nucleic acids of interest were present in the sample.

The various hybridization and capture steps can be performed simultaneously or sequentially, in any convenient order. For example, in embodiments in which capture extenders are employed, each nucleic acid of interest can be hybridized with its corresponding subset of m label extenders and its corresponding subset of n capture extenders, and then the capture extenders can be hybridized with capture probes associated with the solid support.

The methods are useful for multiplex detection of nucleic acids, optionally highly multiplex detection. Thus, the two or more nucleic acids of interest (i.e., the nucleic acids to be detected) optionally comprise five or more, 10 or more, 20 or more, 30 or more, 40 or more, 50 or more, or even 100 or more nucleic acids of interest, while the two or more subsets of m label extenders comprise five or more, 10 or more, 20 or more, 30 or more, 40 or more, 50 or more, or even 100 or more subsets of m label extenders. In embodiments in which capture extenders, particulate solid supports, and/or spatially addressable solid support are used, a like number of subsets of capture extenders, subsets of particles, and/or selected positions on the solid support are provided.

The label probe system optionally includes a preamplifier, an amplification multimer, and a label probe, wherein the preamplifier is capable of hybridizing simultaneously to the at least two of the m label extenders and to a plurality of amplification multimers, and wherein the amplification multimer is capable of hybridizing simultaneously to the preamplifier and to a plurality of label probes. In one class of embodiments, the label probe comprises the label.

In one aspect, the label is a fluorescent label. Detecting the presence of the label on the particles thus comprises detecting a fluorescent signal from the label. The methods can optionally be used to quantitate the amounts of the nucleic acids of interest present in the sample. For example, in one class of embodiments, an intensity of a signal from the label is measured, e.g., for each subset of particles or selected position on the solid support, and correlated with a quantity of the corresponding nucleic acid of interest present.

As noted above, a component of the label probe system is capable of hybridizing simultaneously to at least two of the m label extenders in a subset. Typically, the component of the label probe system that hybridizes to the two or more label extenders is an amplification multimer or preamplifier. Thus, in one aspect, the label probe system comprises an amplification multimer or preamplifier, which amplification multimer or preamplifier is capable of hybridizing to the at least two label extenders, and the label probe system is hybridized to the m label extenders at a hybridization temperature, which hybridization temperature is greater than a melting temperature $T_m$ of a complex between each individual label extender and the amplification multimer or preamplifier. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Each label extender typically comprises a polynucleotide sequence L-1 that is complementary to a polynucleotide sequence in the corresponding nucleic acid of interest and a polynucleotide sequence L-2 that is complementary to a polynucleotide sequence in the component of the label probe system. In one class of embodiments, the m label extenders in a subset each have L-1 5' of L-2 or each have L-1 3' of L-2. The length of L-2 can vary. For example, sequence L-2 can be 20 nucleotides or less in length, e.g., L-2 can be between 9 and 17 nucleotides in length or between 12 and 15 or between 13 and 15 nucleotides in length.

At any of various steps, materials not captured on the solid support are optionally separated from the support. For example, after the nucleic acids, label extenders, optional blocking probes, optional capture extenders, and optional support-bound capture probes are hybridized, the support is optionally washed to remove unbound nucleic acids and probes; after the label extenders and optional amplification multimer are hybridized, the support is optionally washed to remove unbound amplification multimer; and/or after the label probes are hybridized to the amplification multimer, the support is optionally washed to remove unbound label probe prior to detection of the label.

The methods can be used to detect the presence of the nucleic acids of interest in essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen. In one class of embodiments, the two or more nucleic acids of interest comprise two or more mRNAs.

Another general class of embodiments provides a composition for detecting two or more nucleic acids of interest. In one aspect, the composition includes a pooled population of particles. The population comprises two or more subsets of particles, with a plurality of the particles in each subset being distinguishable from a plurality of the particles in every other subset. The particles in each subset have associated therewith a different capture probe. In another aspect, the composition includes a solid support comprising two or more capture probes, wherein each capture probe is provided at a selected position on the solid support.

The composition also includes two or more subsets of n capture extenders, wherein n is at least two, two or more subsets of m label extenders, wherein m is at least two, and a label probe system comprising a label, wherein a component of the label probe system is capable of hybridizing simultaneously to at least two of the m label extenders in a subset. Each subset of n capture extenders is capable of hybridizing to one of the nucleic acids of interest, and the capture extenders in each subset are capable of hybridizing to one of the capture probes and thereby associating each subset of n capture extenders with a selected subset of the particles or with a selected position on the solid support. Similarly, each subset of m label extenders is capable of hybridizing to one of the nucleic acids of interest.

Essentially all of the features noted for the methods above apply to these embodiments as well, as relevant; for example, with respect to composition of the label probe system; type of label; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like. The composition optionally includes at least one of the nucleic acids of interest.

Yet another general class of embodiments provides a kit for detecting two or more nucleic acids of interest. In one aspect, the kit includes a pooled population of particles. The population comprises two or more subsets of particles, with a plurality of the particles in each subset being distinguishable from a plurality of the particles in every other subset. The particles in each subset have associated therewith a different capture probe. In another aspect, the kit includes a solid support comprising two or more capture probes, wherein each capture probe is provided at a selected position on the solid support.

The kit also includes two or more subsets of n capture extenders, wherein n is at least two, two or more subsets of m label extenders, wherein m is at least two, and a label probe system comprising a label, wherein a component of the label probe system is capable of hybridizing simultaneously to at least two of the m label extenders in a subset. Each subset of n capture extenders is capable of hybridizing to one of the nucleic acids of interest, and the capture extenders in each subset are capable of hybridizing to one of the capture probes and thereby associating each subset of n capture extenders with a selected subset of the particles or with a selected position on the solid support. Similarly, each subset of m label extenders is capable of hybridizing to one of the nucleic acids of interest. The components of the kit are packaged in one or more containers.

Essentially all of the features noted for the embodiments above apply to these embodiments as well, as relevant; for example, with respect to composition of the label probe system; type of label; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

Another general class of embodiments provides methods of detecting one or more nucleic acids using a novel label extender configuration. In the methods, a sample comprising or suspected of comprising the nucleic acids of interest, one or more subsets of m label extenders, wherein m is at least two, and a label probe system are provided. Each subset of m label extenders is capable of hybridizing to one of the nucleic acids of interest. The label probe system comprises a label, and a component of the label probe system (e.g., a preamplifier or an amplification multimer) is capable of hybridizing simultaneously to at least two of the m label extenders in a subset. Each label extender comprises a polynucleotide sequence L-1 that is complementary to a polynucleotide sequence in the corresponding nucleic acid of interest and a polynucleotide sequence L-2 that is complementary to a polynucleotide sequence in the component of the label probe system, and the at least two label extenders (e.g., the m label extenders in a subset) each have L-1 5' of L-2 or each have L-1 3' of L-2.

Those nucleic acids of interest present in the sample are captured on a solid support. Each nucleic acid of interest captured on the solid support is hybridized to its corresponding subset of m label extenders, and the label probe system is hybridized to the m label extenders at a hybridization temperature. The hybridization temperature is greater than a melting temperature $T_m$ of a complex between each individual label extender and the component of the label probe system. The presence or absence of the label on the solid support is then detected. Since the label is associated with the nucleic acid(s) of interest via hybridization of the label extenders and label probe system, the presence or absence of the label on the solid support is correlated with the presence or absence of the nucleic acid(s) of interest on the solid support and thus in the original sample.

Typically, the one or more nucleic acids of interest comprise two or more nucleic acids of interest, and the one or more subsets of m label extenders comprise two or more subsets of m label extenders.

As for the methods described above, essentially any suitable solid support can be employed. For example, the solid support can comprise particles such as microspheres, or it can comprise a substantially planar and/or spatially addressable support. Different nucleic acids are optionally captured on different distinguishable subsets of particles or at different positions on a spatially addressable solid support. The nucleic acids of interest can be captured to the solid support by any of a variety of techniques, for example, by binding directly to the solid support or by binding to a moiety bound to the support, or through hybridization to another nucleic acid bound to the solid support. Preferably, the nucleic acids are captured to the solid support through hybridization with capture extenders and capture probes.

In one class of embodiments in which the one or more nucleic acids of interest comprise two or more nucleic acids of interest and the one or more subsets of m label extenders comprise two or more subsets of m label extenders, a pooled population of particles which constitute the solid support is provided. The population comprises two or more subsets of particles, and a plurality of the particles in each subset is distinguishable from a plurality of the particles in every other subset. The particles in each subset have associated therewith a different capture probe.

Two or more subsets of n capture extenders, wherein n is at least two, are also provided. Each subset of n capture extenders is capable of hybridizing to one of the nucleic acids of interest, and the capture extenders in each subset are capable of hybridizing to one of the capture probes, thereby associating each subset of n capture extenders with a selected subset of the particles. Each of the nucleic acids of interest present in the sample is hybridized to its corresponding subset of n capture extenders and the subset of n capture extenders is hybridized to its corresponding capture probe, thereby capturing the nucleic acid on the subset of particles with which the capture extenders are associated.

Typically, in this class of embodiments, at least a portion of the particles from each subset are identified and the presence or absence of the label on those particles is detected. Since a correlation exists between a particular subset of particles and a particular nucleic acid of interest, which subsets of particles have the label present indicates which of the nucleic acids of interest were present in the sample.

In other embodiments in which the one or more nucleic acids of interest comprise two or more nucleic acids of interest and the one or more subsets of m label extenders comprise two or more subsets of m label extenders, the nucleic acids are captured at different positions on a non-particulate, spatially addressable solid support. Thus, in one class of embodiments, the solid support comprises two or more capture probes, wherein each capture probe is provided at a selected position on the solid support. Two or more subsets of n capture extenders, wherein n is at least two, are provided. Each subset of n capture extenders is capable of hybridizing to one of the nucleic acids of interest, and the capture extenders in each subset are capable of hybridizing to one of the capture probes, thereby associating each subset of n capture extenders with a selected position on the solid support. Each of the nucleic acids of interest present in the sample is hybridized to its corresponding subset of n capture extenders and the subset of n capture extenders is hybridized to its corresponding capture probe, thereby capturing the nucleic acid on the solid support at the selected position with which the capture extenders are associated.

Typically, in this class of embodiments, the presence or absence of the label at the selected positions on the solid support is detected. Since a correlation exists between a particular position on the support and a particular nucleic acid of interest, which positions have a label present indicates which of the nucleic acids of interest were present in the sample.

Essentially all of the features noted for the methods above apply to these embodiments as well, as relevant; for example, with respect to composition of the label probe system; type of label; type of solid support; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

Another general class of embodiments provides a composition for detecting one or more nucleic acids of interest. The composition includes a solid support comprising one or more capture probes, one or more subsets of n capture extenders, wherein n is at least two, one or more subsets of m label extenders, wherein m is at least two, and a label probe system comprising a label. Each subset of n capture extenders is capable of hybridizing to one of the nucleic acids of interest, and the capture extenders in each subset are capable of hybridizing to one of the capture probes and thereby associating each subset of n capture extenders with the solid support. Each subset of m label extenders is capable of hybridizing to one of the nucleic acids of interest. A component of the label probe system (e.g., a preamplifier or amplification multimer) is capable of hybridizing simultaneously to at least two of the m label extenders in a subset. Each label extender comprises a polynucleotide sequence L-1 that is complementary to a polynucleotide sequence in the corresponding nucleic acid of interest and a polynucleotide sequence L-2 that is complementary to a polynucleotide sequence in the component of the label probe system, and the m label extenders in a subset each have L-1 5' of L-2 or each have L-1 3' of L-2.

In one class of embodiments, the one or more nucleic acids of interest comprise two or more nucleic acids of interest, the one or more subsets of n capture extenders comprise two or more subsets of n capture extenders, the one or more subsets of m label extenders comprise two or more subsets of m label extenders, and the solid support comprises a pooled population of particles. The population comprises two or more subsets of particles. A plurality of the particles in each subset are distinguishable from a plurality of the particles in every other subset, and the particles in each subset have associated therewith a different capture probe. The capture extenders in each subset are capable of hybridizing to one of the capture probes and thereby associating each subset of n capture extenders with a selected subset of the particles.

In another class of embodiments, the one or more nucleic acids of interest comprise two or more nucleic acids of interest, the one or more subsets of n capture extenders comprise two or more subsets of n capture extenders, the one or more subsets of m label extenders comprise two or more subsets of m label extenders, and the solid support comprises two or more capture probes, wherein each capture probe is provided at a selected position on the solid support. The capture extenders in each subset are capable of hybridizing to one of the capture probes and thereby associating each subset of n capture extenders with a selected position on the solid support.

Essentially all of the features noted for the embodiments above apply to these embodiments as well, as relevant; for example, with respect to composition of the label probe system; type of label; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

For example, the label probe system can include an amplification multimer or preamplifier, which amplification multimer or preamplifier is capable of hybridizing to the at least two label extenders. The composition optionally includes one or more of the nucleic acids of interest, wherein each nucleic acid of interest is hybridized to its corresponding subset of m label extenders and to its corresponding subset of n capture extenders, which in turn is hybridized to its corresponding capture probe. The amplification multimer or preamplifier is hybridized to the m label extenders. The composition is maintained at a hybridization temperature that is greater than a melting temperature $T_m$ of a complex between each individual label extender and the amplification multimer or preamplifier (e.g., about 5° C. or more, about 7° C. or more, about 10° C. or more, about 12° C. or more, about 15° C. or more, about 17° C. or more, or about 20° C. or more greater than the $T_m$).

Yet another general class of embodiments provides a kit for detecting one or more nucleic acids of interest. The kit includes a solid support comprising one or more capture probes, one or more subsets of n capture extenders, wherein n is at least two, one or more subsets of m label extenders, wherein m is at least two, and a label probe system comprising a label. Each subset of n capture extenders is capable of hybridizing to one of the nucleic acids of interest, and the capture extenders in each subset are capable of hybridizing to one of the capture probes and thereby associating each subset of n capture extenders with the solid support. Each subset of m label extenders is capable of hybridizing to one of the nucleic acids of interest. A component of the label probe system (e.g., a preamplifier or amplification multimer) is capable of hybridizing simultaneously to at least two of the m label extenders in a subset. Each label extender comprises a polynucleotide sequence L-1 that is complementary to a polynucleotide sequence in the corresponding nucleic acid of interest and a polynucleotide sequence L-2 that is complementary to a polynucleotide sequence in the component of the label probe system, and the m label extenders in a subset each have L-1 5' of L-2 or each have L-1 3' of L-2. The components of the kit are packaged in one or more containers. The kit optionally also includes instructions for using the kit to capture and detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to composition of the label probe system; type of label; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

For example, in one class of embodiments, the one or more nucleic acids of interest comprise two or more nucleic acids of interest, the one or more subsets of n capture extenders comprise two or more subsets of n capture extenders, the one or more subsets of m label extenders comprise two or more subsets of m label extenders, and the solid support comprises a pooled population of particles. The population comprises two or more subsets of particles. A plurality of the particles in each subset are distinguishable from a plurality of the particles in every other subset, and the particles in each subset have associated therewith a different capture probe. The capture extenders in each subset are capable of hybridizing to one of the capture probes and thereby associating each subset of n capture extenders with a selected subset of the particles.

In another class of embodiments, the one or more nucleic acids of interest comprise two or more nucleic acids of interest, the one or more subsets of n capture extenders comprise two or more subsets of n capture extenders, the one or more subsets of m label extenders comprise two or more subsets of m label extenders, and the solid support comprises two or more capture probes, wherein each capture probe is provided at a selected position on the solid support. The capture extenders in each subset are capable of hybridizing to one of the capture probes and thereby associating each subset of n capture extenders with a selected position on the solid support.

Yet another general class of embodiments provides methods of capturing a label to a first nucleic acid of interest in a multiplex assay in which two or more nucleic acids of interest are to be detected. In the methods, a sample comprising the first nucleic acid of interest and also comprising or suspected of comprising one or more other nucleic acids of interest is provided. A first subset of m label extenders, wherein m is at least two, and a label probe system comprising the label are also provided. The first subset of m label extenders is capable of hybridizing to the first nucleic acid of interest, and a component of the label probe system is capable of hybridizing simultaneously to at least two of the m label extenders in the first subset. The first nucleic acid of interest is hybridized to the first subset of m label extenders, and the label probe system is hybridized to the m label extenders, thereby capturing the label to the first nucleic acid of interest.

Essentially all of the features noted for the embodiments above apply to these methods as well, as relevant; for example, with respect to configuration of the label extenders, number of label extenders per subset, composition of the label probe system, type of label, number of nucleic acids of interest, source of the sample and/or nucleic acids, and/or the like.

Yet another general class of embodiments provides methods of capturing a label to a nucleic acid of interest. In the methods, m label extenders, wherein m is at least two, are provided. The m label extenders are capable of hybridizing to the nucleic acid of interest. A label probe system comprising the label is also provided. A component of the label probe system is capable of hybridizing simultaneously to at least two of the m label extenders. Each label extender comprises a polynucleotide sequence L-1 that is complementary to a polynucleotide sequence in the nucleic acid of interest and a polynucleotide sequence L-2 that is complementary to a polynucleotide sequence in the component of the label probe system, and the m label extenders each have L-1 5' of L-2 or wherein the m label extenders each have L-1 3' of L-2. The nucleic acid of interest is hybridized to the m label extenders, and the label probe system is hybridized to the m label extenders at a hybridization temperature, thereby capturing the label to the nucleic acid of interest. Preferably, the hybridization temperature is greater than a melting temperature $T_m$ of a complex between each individual label extender and the component of the label probe system.

Essentially all of the features noted for the embodiments above apply to these methods as well, as relevant; for example, with respect to configuration of the label extenders, number of label extenders per subset, composition of the label probe system, type of label, and/or the like.

Figure 1:
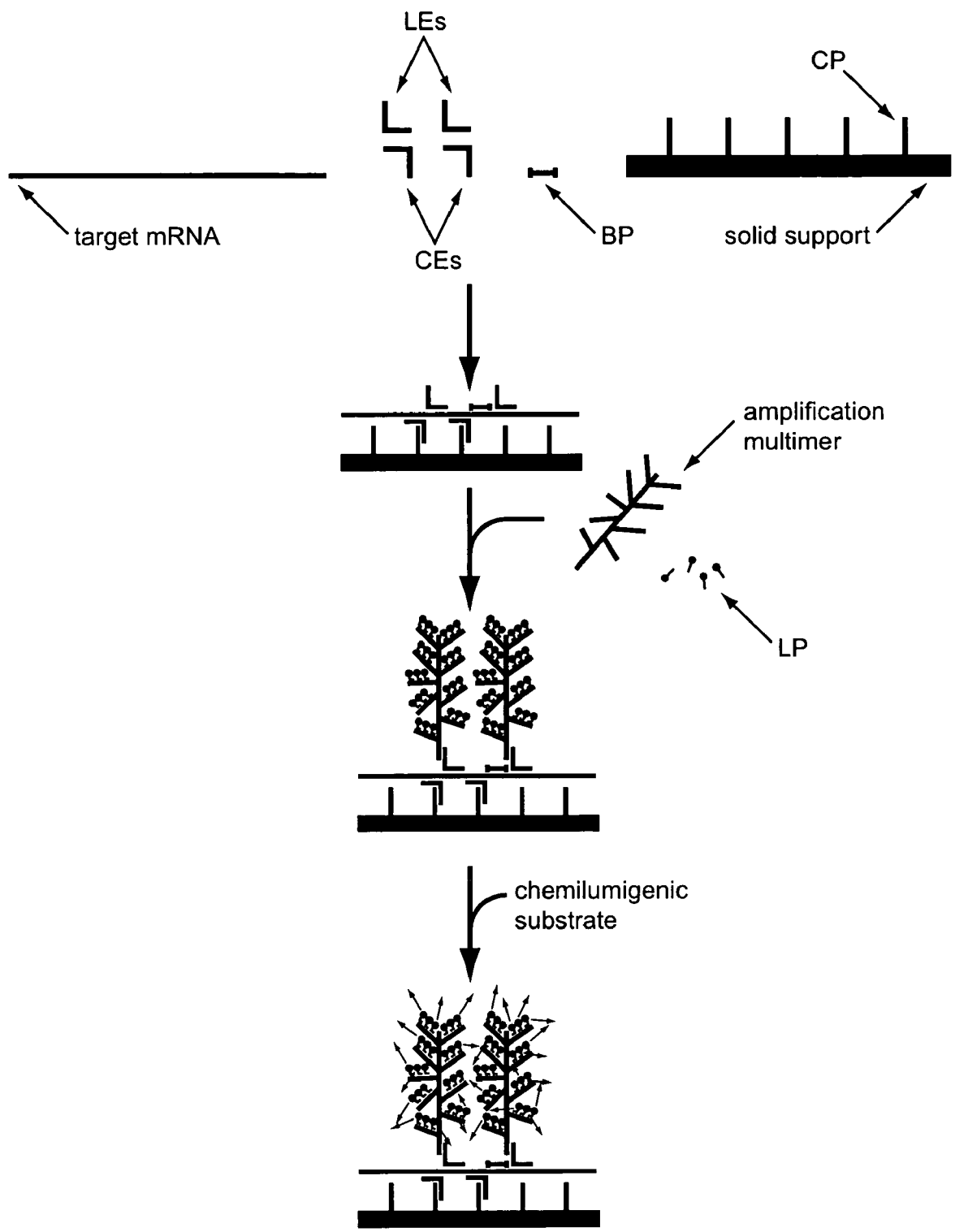
FIG. 1 schematically illustrates a typical standard bDNA assay.
Figure 2E:
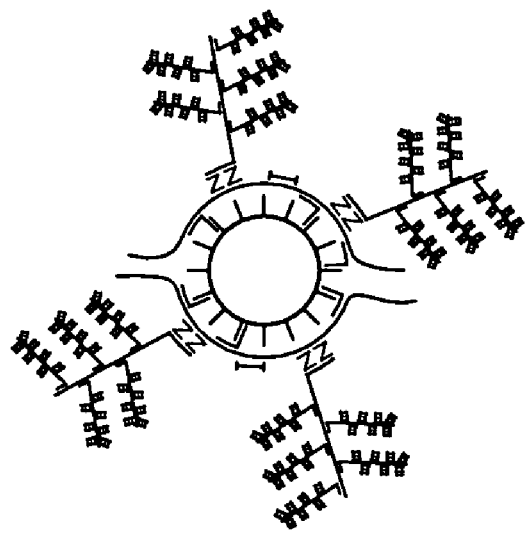
FIG. 2 Panels A-E schematically depict a multiplex nucleic acid detection assay, in which the nucleic acids of interest are captured on distinguishable subsets of microspheres and then detected.
Figure 2E:
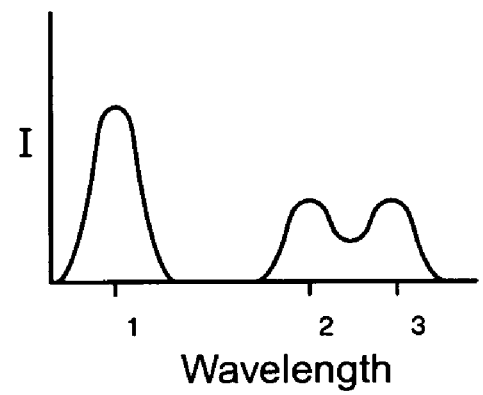
Figure 2E:
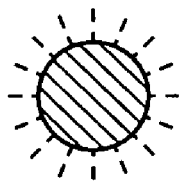
Figure 2E:
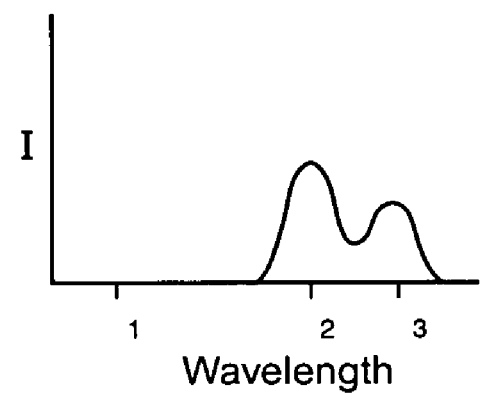
Figure 2E:
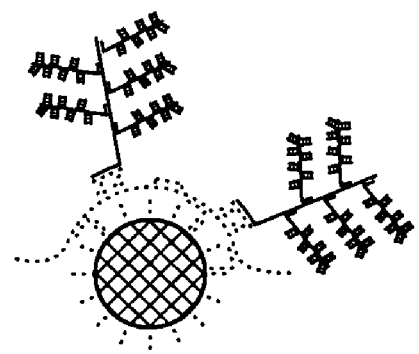
Figure 2E:
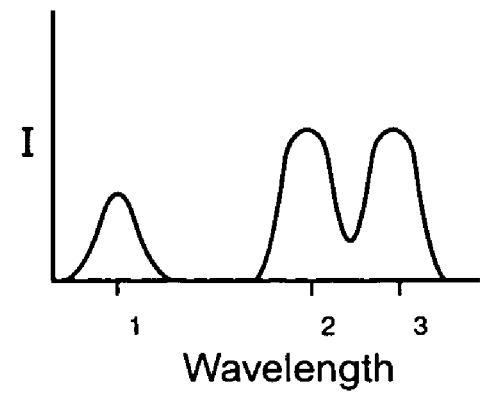

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, N.Y.), as well as in Ausubel, infra.

The "$T_m$" (melting temperature) of a nucleic acid duplex under specified conditions (e.g., relevant assay conditions) is the temperature at which half of the base pairs in a population of the duplex are disassociated and half are associated. The $T_m$ for a particular duplex can be calculated and/or measured, e.g., by obtaining a thermal denaturation curve for the duplex (where the $T_m$ is the temperature corresponding to the midpoint in the observed transition from double-stranded to single-stranded form).

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "capture extender" or "CE" is a polynucleotide that is capable of hybridizing to a nucleic acid of interest and to a capture probe. The capture extender typically has a first polynucleotide sequence C-1, which is complementary to the capture probe, and a second polynucleotide sequence C-3, which is complementary to a polynucleotide sequence of the nucleic acid of interest. Sequences C-1 and C-3 are typically not complementary to each other. The capture extender is preferably single-stranded.

A "capture probe" or "CP" is a polynucleotide that is capable of hybridizing to at least one capture extender and that is tightly bound (e.g., covalently or noncovalently, directly or through a linker, e.g., streptavidin-biotin or the like) to a solid support, a spatially addressable solid support, a slide, a particle, a microsphere, or the like. The capture probe typically comprises at least one polynucleotide sequence C-2 that is complementary to polynucleotide sequence C-1 of at least one capture extender. The capture probe is preferably single-stranded.

A "label extender" or "LE" is a polynucleotide that is capable of hybridizing to a nucleic acid of interest and to a label probe system. The label extender typically has a first polynucleotide sequence L-1, which is complementary to a polynucleotide sequence of the nucleic acid of interest, and a second polynucleotide sequence L-2, which is complementary to a polynucleotide sequence of the label probe system (e.g., L-2 can be complementary to a polynucleotide sequence of an amplification multimer, a preamplifier, a label probe, or the like). The label extender is preferably single-stranded.

A "label" is a moiety that facilitates detection of a molecule. Common labels in the context of the present invention include fluorescent, luminescent, light-scattering, and/or calorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "label probe system" comprises one or more polynucleotides that collectively comprise a label and at least two polynucleotide sequences M-1, each of which is capable of hybridizing to a label extender. The label provides a signal, directly or indirectly. Polynucleotide sequence M-1 is typically complementary to sequence L-2 in the label extenders. The at least two polynucleotide sequences M-1 are optionally identical sequences or different sequences. The label probe system can include a plurality of label probes (e.g., a plurality of identical label probes) and an amplification multimer; it optionally also includes a preamplifier or the like, or optionally includes only label probes, for example.

An "amplification multimer" is a polynucleotide comprising a plurality of polynucleotide sequences M-2, typically (but not necessarily) identical polynucleotide sequences M-2. Polynucleotide sequence M-2 is complementary to a polynucleotide sequence in the label probe. The amplification multimer also includes at least one polynucleotide sequence that is capable of hybridizing to a label extender or to a nucleic acid that hybridizes to the label extender, e.g., a preamplifier. For example, the amplification multimer optionally includes at least one (and preferably at least two) polynucleotide sequence(s) M-1, optionally identical sequences M-1; polynucleotide sequence M-1 is typically complementary to polynucleotide sequence L-2 of the label extenders. Similarly, the amplification multimer optionally includes at least one polynucleotide sequence that is complementary to a polynucleotide sequence in a preamplifier. The amplification multimer can be, e.g., a linear or a branched nucleic acid. As noted for all polynucleotides, the amplification multimer can include modified nucleotides and/or nonstandard internucleotide linkages as well as standard deoxyribonucleotides, ribonucleotides, and/or phosphodiester bonds. Suitable amplification multimers are described, for example, in U.S. Pat. No. 5,635,352, U.S. Pat. No. 5,124,246, U.S. Pat. No. 5,710,264, and U.S. Pat. No. 5,849,481.

A "label probe" or "LP" is a single-stranded polynucleotide that comprises a label (or optionally that is configured to bind to a label) that directly or indirectly provides a detectable signal. The label probe typically comprises a polynucleotide sequence that is complementary to the repeating polynucleotide sequence M-2 of the amplification multimer; however, if no amplification multimer is used in the bDNA assay, the label probe can, e.g., hybridize directly to a label extender.

A "preamplifier" is a nucleic acid that serves as an intermediate between one or more label extenders and amplification multimers. Typically, the preamplifier is capable of hybridizing simultaneously to at least two label extenders and to a plurality of amplification multimers.

A "microsphere" is a small spherical, or roughly spherical, particle. A microsphere typically has a diameter less than about 1000 micrometers (e.g., less than about 100 micrometers, optionally less than about 10 micrometers).

A "microorganism" is an organism of microscopic or submicroscopic size. Examples include, but are not limited to, bacteria, fungi, yeast, protozoans, microscopic algae (e.g., unicellular algae), viruses (which are typically included in this category although they are incapable of growth and reproduction outside of host cells), subviral agents, viroids, and mycoplasma.

A first polynucleotide sequence that is located "5' of" a second polynucleotide sequence on a nucleic acid strand is positioned closer to the 5' terminus of the strand than is the second polynucleotide sequence. Similarly, a first polynucleotide sequence that is located "3' of" a second polynucleotide sequence on a nucleic acid strand is positioned closer to the 3' terminus of the strand than is the second polynucleotide sequence.

A variety of additional terms are defined or otherwise characterized herein.

DETAILED DESCRIPTION

The present invention provides methods, compositions, and kits for detection of nucleic acids, particularly multiplex detection. Nucleic acids of interest are captured to a solid support and then detected, preferably in a branched-chain DNA assay.

Branched-chain DNA (bDNA) signal amplification technology has been used, e.g., to detect and quantify mRNA transcripts in cell lines and to determine viral loads in blood. The bDNA assay is a sandwich nucleic acid hybridization procedure that enables direct measurement of mRNA expression, e.g., from crude cell lysate. It provides direct quantification of nucleic acid molecules at physiological levels. Several advantages of the technology distinguish it from other DNA/RNA amplification technologies, including linear amplification, good sensitivity and dynamic range, great precision and accuracy, simple sample preparation procedure, and reduced sample-to-sample variation.

In brief, in a typical bDNA assay for gene expression analysis (FIG. 1), a target mRNA whose expression is to be detected is released from cells and captured by a Capture Probe (CP) on a solid surface (e.g., a well of a microtiter plate) through synthetic oligonucleotide probes called Capture Extenders (CEs). Each capture extender has a first polynucleotide sequence that can hybridize to the target mRNA and a second polynucleotide sequence that can hybridize to the capture probe. Typically, two or more capture extenders are used. Probes of another type, called Label Extenders (LEs), hybridize to different sequences on the target mRNA and to sequences on an amplification multimer. Additionally, Blocking Probes (BPs), which hybridize to regions of the target mRNA not occupied by CEs or LEs, are often used to reduce non-specific target probe binding. A probe set for a given mRNA thus consists of CEs, LEs, and optionally BPs for the target mRNA. The CEs, LEs, and BPs are complementary to nonoverlapping sequences in the target mRNA, and are typically, but not necessarily, contiguous.

Signal amplification begins with the binding of the LEs to the target mRNA. An amplification multimer is then typically hybridized to the LEs. The amplification multimer has multiple copies of a sequence that is complementary to a label probe (it is worth noting that the amplification multimer is typically, but not necessarily, a branched-chain nucleic acid; for example, the amplification multimer can be a branched, forked, or comb-like nucleic acid or a linear nucleic acid). A label, for example, alkaline phosphatase, is covalently attached to each label probe. (Alternatively, the label can be noncovalently bound to the label probes.) In the final step, labeled complexes are detected, e.g., by the alkaline phosphatase-mediated degradation of a chemilumigenic substrate, e.g., dioxetane. Luminescence is reported as relative light unit (RLUs) on a microplate reader. The amount of chemiluminescence is proportional to the level of mRNA expressed from the target gene.

In the preceding example, the amplification multimer and the label probes comprise a label probe system. In another example, the label probe system also comprises a preamplifier, e.g., as described in U.S. Pat. No. 5,635,352 and U.S. Pat. No. 5,681,697, which further amplifies the signal from a single target mRNA. In yet another example, the label extenders hybridize directly to the label probes and no amplification multimer or preamplifier is used, so the signal from a single target mRNA molecule is only amplified by the number of distinct label extenders that hybridize to that mRNA.

Basic bDNA assays have been well described. See, e.g., U.S. Pat. No. 4,868,105 to Urdea et al. entitled "Solution phase nucleic acid sandwich assay"; U.S. Pat. No. 5,635,352 to Urdea et al. entitled "Solution phase nucleic acid sandwich assays having reduced background noise"; U.S. Pat. No. 5,681,697 to Urdea et al. entitled "Solution phase nucleic acid sandwich assays having reduced background noise and kits therefor"; U.S. Pat. No. 5,124,246 to Urdea et al. entitled "Nucleic acid multimers and amplified nucleic acid hybridization assays using same"; U.S. Pat. No. 5,624,802 to Urdea et al. entitled "Nucleic acid multimers and amplified nucleic acid hybridization assays using same"; U.S. Pat. No. 5,849,481 to Urdea et al. entitled "Nucleic acid hybridization assays employing large comb-type branched polynucleotides"; U.S. Pat. No. 5,710,264 to Urdea et al. entitled "Large comb type branched polynucleotides"; U.S. Pat. No. 5,594,118 to Urdea and Horn entitled "Modified N-4 nucleotides for use in amplified nucleic acid hybridization assays"; U.S. Pat. No. 5,093,232 to Urdea and Horn entitled "Nucleic acid probes"; U.S.

Pat. No. 4,910,300 to Urdea and Horn entitled "Method for making nucleic acid probes"; U.S. Pat. No. 5,359,100; U.S. Pat. No. 5,571,670; U.S. Pat. No. 5,614,362; U.S. Pat. No. 6,235,465; U.S. Pat. No. 5,712,383; U.S. Pat. No. 5,747,244; U.S. Pat. No. 6,232,462; U.S. Pat. No. 5,681,702; U.S. Pat. No. 5,780,610; U.S. Pat. No. 5,780,227 to Sheridan et al. entitled "Oligonucleotide probe conjugated to a purified hydrophilic alkaline phosphatase and uses thereof"; U.S. patent application Publication No. US2002172950 by Kenny et al. entitled "Highly sensitive gene detection and localization using in situ branched-DNA hybridization"; Wang et al. (1997) "Regulation of insulin preRNA splicing by glucose" Proc Nat Acad Sci USA 94:4360-4365; Collins et al. (1998) "Branched DNA (bDNA) technology for direct quantification of nucleic acids: Design and performance" in Gene Quantification, F Ferre, ed.; and Wilber and Urdea (1998) "Quantification of HCV RNA in clinical specimens by branched DNA (bDNA) technology" Methods in Molecular Medicine: Hepatitis C 19:71-78. In addition, kits for performing basic bDNA assays (QuantiGene™ kits, comprising instructions and reagents such as amplification multimers, alkaline phosphatase labeled label probes, chemilumigenic substrate, capture probes immobilized on a solid support, and the like) are commercially available, e.g., from Panomics, Inc. (on the world wide web at (www.) panomics.com). Software for designing probe sets for a given mRNA target (i.e., for designing the regions of the CEs, LEs, and optionally BPs that are complementary to the target) is also commercially available (e.g., ProbeDesigner™ from Panomics, Inc.; see also Bushnell et al. (1999) "ProbeDesigner: for the design of probe sets for branched DNA (bDNA) signal amplification assays Bioinformatics 15:348-55). The basic bDNA assay, however, permits detection of only a single target nucleic acid per assay, while, as described above, detection of multiple nucleic acids is frequently desirable.

Among other aspects, the present invention provides multiplex bDNA assays that can be used for simultaneous detection of two or more target nucleic acids. Similarly, one aspect of the present invention provides bDNA assays, singleplex or multiplex, that have reduced background from nonspecific hybridization events.

In general, in the assays of the invention, two or more label extenders are used to capture a single component of the label probe system (e.g., a preamplifier or amplification multimer). The assay temperature and the stability of the complex between a single LE and the component of the label probe system (e.g., the preamplifier or amplification multimer) can be controlled such that binding of a single LE to the component is not sufficient to stably associate the component with a nucleic acid to which the LE is bound, whereas simultaneous binding of two or more LEs to the component can capture it to the nucleic acid. Requiring such cooperative hybridization of multiple LEs for association of the label probe system with the nucleic acid(s) of interest results in high specificity and low background from cross-hybridization of the LEs with other, non-target nucleic acids.

For an assay to achieve high specificity and sensitivity, it preferably has a low background, resulting, e.g., from minimal cross-hybridization. Such low background and minimal cross-hybridization are typically substantially more difficult to achieve in a multiplex assay than a single-plex assay, because the number of potential nonspecific interactions are greatly increased in a multiplex assay due to the increased number of probes used in the assay (e.g., the greater number of CEs and LEs). Requiring multiple simultaneous LE-label probe system component interactions for the capture of the label probe system to a target nucleic acid minimizes the chance that nonspecific capture will occur, even when some nonspecific CE-LE or LE-CP interactions, for example, do occur. This reduction in background through minimization of undesirable cross-hybridization events thus facilitates multiplex detection of the nucleic acids of interest.

The methods of the invention can be used, for example, for multiplex detection of two or more nucleic acids simultaneously, from even complex samples, without requiring prior purification of the nucleic acids. In one aspect, the methods involve capture of the nucleic acids to particles (e.g., distinguishable subsets of microspheres), while in another aspect, the nucleic acids are captured to a spatially addressable solid support. Compositions, kits, and systems related to the methods are also provided.

Methods

As noted, one aspect of the invention provides multiplex nucleic acid assays. Thus, one general class of embodiments includes methods of detecting two or more nucleic acids of interest. In the methods, a sample comprising or suspected of comprising the nucleic acids of interest, two or more subsets of m label extenders, wherein m is at least two, and a label probe system are provided. Each subset of m label extenders is capable of hybridizing to one of the nucleic acids of interest. The label probe system comprises a label, and a component of the label probe system is capable of hybridizing simultaneously to at least two of the m label extenders in a subset.

Those nucleic acids of interest present in the sample are captured on a solid support. Each nucleic acid of interest captured on the solid support is hybridized to its corresponding subset of m label extenders, and the label probe system is hybridized to the m label extenders. The presence or absence of the label on the solid support is then detected. Since the label is associated with the nucleic acid(s) of interest via hybridization of the label extenders and label probe system, the presence or absence of the label on the solid support is correlated with the presence or absence of the nucleic acid(s) of interest on the solid support and thus in the original sample.

Essentially any suitable solid support can be employed in the methods. For example, the solid support can comprise particles such as microspheres, or it can comprise a substantially planar and/or spatially addressable support. Different nucleic acids are optionally captured on different distinguishable subsets of particles or at different positions on a spatially addressable solid support. The nucleic acids of interest can be captured to the solid support by any of a variety of techniques, for example, by binding directly to the solid support or by binding to a moiety bound to the support, or through hybridization to another nucleic acid bound to the solid support. Preferably, the nucleic acids are captured to the solid support through hybridization with capture extenders and capture probes.

In one class of embodiments, a pooled population of particles which constitute the solid support is provided. The population comprises two or more subsets of particles, and a plurality of the particles in each subset is distinguishable from a plurality of the particles in every other subset. (Typically, substantially all of the particles in each subset are distinguishable from substantially all of the particles in every other subset.) The particles in each subset have associated therewith a different capture probe.

Two or more subsets of n capture extenders, wherein n is at least two, are also provided. Each subset of n capture extenders is capable of hybridizing to one of the nucleic acids of interest, and the capture extenders in each subset are capable of hybridizing to one of the capture probes, thereby associating each subset of n capture extenders with a selected subset of the particles. Each of the nucleic acids of interest present in the sample is hybridized to its corresponding subset of n capture extenders and the subset of n capture extenders is hybridized to its corresponding capture probe, thereby capturing the nucleic acid on the subset of particles with which the capture extenders are associated.

Typically, in this class of embodiments, at least a portion of the particles from each subset are identified and the presence or absence of the label on those particles is detected. Since a correlation exists between a particular subset of particles and a particular nucleic acid of interest, which subsets of particles have the label present indicates which of the nucleic acids of interest were present in the sample.

Essentially any suitable particles, e.g., particles having distinguishable characteristics and to which capture probes can be attached, can be used. For example, in one preferred class of embodiments, the particles are microspheres. The microspheres of each subset can be distinguishable from those of the other subsets, e.g., on the basis of their fluorescent emission spectrum, their diameter, or a combination thereof. For example, the microspheres of each subset can be labeled with a unique fluorescent dye or mixture of such dyes, quantum dots with distinguishable emission spectra, and/or the like. As another example, the particles of each subset can be identified by an optical barcode, unique to that subset, present on the particles.

The particles optionally have additional desirable characteristics. For example, the particles can be magnetic or paramagnetic, which provides a convenient means for separating the particles from solution, e.g., to simplify separation of the particles from any materials not bound to the particles.

In other embodiments, the nucleic acids are captured at different positions on a non-particulate, spatially addressable solid support. Thus, in one class of embodiments, the solid support comprises two or more capture probes, wherein each capture probe is provided at a selected position on the solid support. Two or more subsets of n capture extenders, wherein n is at least two, are provided. Each subset of n capture extenders is capable of hybridizing to one of the nucleic acids of interest, and the capture extenders in each subset are capable of hybridizing to one of the capture probes, thereby associating each subset of n capture extenders with a selected position on the solid support. Each of the nucleic acids of interest present in the sample is hybridized to its corresponding subset of n capture extenders and the subset of n capture extenders is hybridized to its corresponding capture probe, thereby capturing the nucleic acid on the solid support at the selected position with which the capture extenders are associated.

Typically, in this class of embodiments, the presence or absence of the label at the selected positions on the solid support is detected. Since a correlation exists between a particular position on the support and a particular nucleic acid of interest, which positions have a label present indicates which of the nucleic acids of interest were present in the sample.

The solid support typically has a planar surface and is typically rigid, but essentially any spatially addressable solid support can be adapted to the practice of the present invention. Exemplary materials for the solid support include, but are not limited to, glass, silicon, silica, quartz, plastic, polystyrene, nylon, and nitrocellulose. As just one example, an array of capture probes can be formed at selected positions on a glass slide as the solid support.

In any of the embodiments described herein in which capture extenders are utilized to capture the nucleic acids to the solid support, n, the number of capture extenders in a subset, is at least one, preferably at least two, and more preferably at least three. n can be at least four or at least five or more. Typically, but not necessarily, n is at most ten. For example, n can be between three and ten, e.g., between five and ten or between five and seven, inclusive. Use of fewer capture extenders can be advantageous, for example, in embodiments in which nucleic acids of interest are to be specifically detected from samples including other nucleic acids with sequences very similar to that of the nucleic acids of interest. In other embodiments (e.g., embodiments in which capture of as much of the nucleic acid as possible is desired), however, n can be more than 10, e.g., between 20 and 50. n can be the same for all of the subsets of capture extenders, but it need not be; for example, one subset can include three capture extenders while another subset includes five capture extenders. The n capture extenders in a subset preferably hybridize to nonoverlapping polynucleotide sequences in the corresponding nucleic acid of interest. The nonoverlapping polynucleotide sequences can, but need not be, consecutive within the nucleic acid of interest.

Each capture extender is capable of hybridizing to its corresponding capture probe. The capture extender typically includes a polynucleotide sequence C-1 that is complementary to a polynucleotide sequence C-2 in its corresponding capture probe. Capture of the nucleic acids of interest via hybridization to the capture extenders and capture probes optionally involves cooperative hybridization. In one aspect, the capture extenders and capture probes are configured as described in U.S. patent application 60/680,976 filed May 12, 2005 by Luo et al., entitled "Multiplex branched-chain DNA assays."

The capture probe can include polynucleotide sequence in addition to C-2, or C-2 can comprise the entire polynucleotide sequence of the capture probe. For example, each capture probe optionally includes a linker sequence between the site of attachment of the capture probe to the particles and sequence C-2 (e.g., a linker sequence containing 8 Ts, as just one possible example).

The methods are useful for multiplex detection of nucleic acids, optionally highly multiplex detection. Thus, the two or more nucleic acids of interest (i.e., the nucleic acids to be detected) optionally comprise five or more, 10 or more, 20 or more, 30 or more, 40 or more, 50 or more, or even 100 or more nucleic acids of interest, while the two or more subsets of m label extenders comprise five or more, 10 or more, 20 or more, 30 or more, 40 or more, 50 or more, or even 100 or more subsets of m label extenders. In embodiments in which capture extenders, particulate solid supports, and/or spatially addressable solid support are used, a like number of subsets of capture extenders, subsets of particles, and/or selected positions on the solid support are provided.

The label probe system optionally includes an amplification multimer and a plurality of label probes, wherein the amplification multimer is capable of hybridizing to the label extenders and to a plurality of label probes. In another aspect, the label probe system includes a preamplifier, a plurality of amplification multimers, and a plurality of label probes, wherein the preamplifier hybridizes to the label extenders, and the amplification multimers hybridize to the preamplifier and to the plurality of label probes. As another example, the label probe system can include only label probes, which hybridize directly to the label extenders. In one class of embodiments, the label probe comprises the label, e.g., a covalently attached label. In other embodiments, the label probe is configured to bind a label; for example, a biotinylated label probe can bind to a streptavidin-associated label.

The label can be essentially any convenient label that directly or indirectly provides a detectable signal. In one aspect, the label is a fluorescent label (e.g., a fluorophore or quantum dot). Detecting the presence of the label on the particles thus comprises detecting a fluorescent signal from the label. In embodiments in which the solid support comprises particles, fluorescent emission by the label is typically distinguishable from any fluorescent emission by the particles, e.g., microspheres, and many suitable fluorescent label-fluorescent microsphere combinations are possible. As other examples, the label can be a luminescent label, a light-scattering label (e.g., colloidal gold particles), or an enzyme (e.g., HRP).

As noted above, a component of the label probe system is capable of hybridizing simultaneously to at least two of the m label extenders in a subset. Typically, the component of the label probe system that hybridizes to the two or more label extenders is an amplification multimer or preamplifier. Preferably, binding of a single label extender to the component of the label probe system (e.g., the amplification multimer or preamplifier) is insufficient to capture the label probe system to the nucleic acid of interest to which the label extender binds. Thus, in one aspect, the label probe system comprises an amplification multimer or preamplifier, which amplification multimer or preamplifier is capable of hybridizing to the at least two label extenders, and the label probe system (or the component thereof) is hybridized to the m label extenders at a hybridization temperature, which hybridization temperature is greater than a melting temperature $T_m$ of a complex between each individual label extender and the amplification multimer or preamplifier. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$. It is worth noting that the hybridization temperature can be the same or different than the temperature at which the label extenders and optional capture extenders are hybridized to the nucleic acids of interest.

Each label extender typically includes a polynucleotide sequence L-1 that is complementary to a polynucleotide sequence in the corresponding nucleic acid of interest and a polynucleotide sequence L-2 that is complementary to a polynucleotide sequence in the component of the label probe system (e.g., the preamplifier or amplification multimer). It will be evident that the amount of overlap between each individual label extender and the component of the label probe system (i.e., the length of L-2 and M-1) affects the $T_m$ of the complex between the label extender and the component, as does, e.g., the GC base content of sequences L-2 and M-1. Optionally, all the label extenders have the same length sequence L-2 and/or identical polynucleotide sequences L-2. Alternatively, different label extenders can have different length and/or sequence polynucleotide sequences L-2. It will also be evident that the number of label extenders required for stable capture of the component to the nucleic acid of interest depends, in part, on the amount of overlap between the label extenders and the component (i.e., the length of L-2 and M-1).

Stable capture of the component of the label probe system by the at least two label extenders, e.g., while minimizing capture of extraneous nucleic acids, can be achieved, for example, by balancing the number of label extenders that bind to the component, the amount of overlap between the label extenders and the component (the length of L-2 and M-1), and/or the stringency of the conditions under which the label extenders and the component are hybridized.

Appropriate combinations of the amount of complementarity between the label extenders and the component of the label probe system, number of label extenders binding to the component, and stringency of hybridization can, for example, be determined experimentally by one of skill in the art. For example, a particular number of label extenders and a particular set of hybridization conditions can be selected, while the number of nucleotides of complementarity between the label extenders and the component is varied until hybridization of the label extenders to a nucleic acid captures the component to the nucleic acid while hybridization of a single label extender does not efficiently capture the component. Stringency can be controlled, for example, by controlling the formamide concentration, chaotropic salt concentration, salt concentration, pH, organic solvent content, and/or hybridization temperature.

As noted, the $T_m$ of any nucleic acid duplex can be directly measured, using techniques well known in the art. For example, a thermal denaturation curve can be obtained for the duplex, the midpoint of which corresponds to the $T_m$. It will be evident that such denaturation curves can be obtained under conditions having essentially any relevant pH, salt concentration, solvent content, and/or the like.

The $T_m$ for a particular duplex (e.g., an approximate $T_m$) can also be calculated. For example, the $T_m$ for an oligonucleotide-target duplex can be estimated using the following algorithm, which incorporates nearest neighbor thermodynamic parameters: Tm (Kelvin)=$\Delta H°/(\Delta S°+R \ln C_t)$, where the changes in standard enthalpy ($\Delta H°$) and entropy ($\Delta S°$) are calculated from nearest neighbor thermodynamic parameters (see, e.g., SantaLucia (1998) "A unified view of polymer, dumbbell, and oligonucleotide DNA nearest-neighbor thermodynamics" Proc. Natl. Acad. Sci. USA 95:1460-1465, Sugimoto et al. (1996) "Improved thermodynamic parameters and helix initiation factor to predict stability of DNA duplexes" Nucleic Acids Research 24: 4501-4505, Sugimoto et al. (1995) "Thermodynamic parameters to predict stability of RNA/DNA hybrid duplexes" Biochemistry 34:11211-11216, and et al. (1998) "Thermodynamic parameters for an expanded nearest-neighbor model for formation of RNA duplexes with Watson-Crick base pairs" Biochemistry 37: 14719-14735), R is the ideal gas constant (1.987 cal·K$^{-1}$ mole$^{-1}$), and $C_t$ is the molar concentration of the oligonucleotide. The calculated $T_m$ is optionally corrected for salt concentration, e.g., Na$^+$ concentration, using the formula $1/T_m$ (Na$^+$)=$1/T_m$(1M)+(4.29f(G·C)−3.95)×10$^{-5}$ ln [Na$^+$]+9.40× 10$^{-6}$ ln$^2$[Na$^+$]. See, e.g., Owczarzy et al. (2004) "Effects of Sodium Ions on DNA Duplex Oligomers: Improved Predictions of Melting Temperatures" Biochemistry 43:3537-3554 for further details. A Web calculator for estimating $T_m$ using the above algorithms is available on the Internet at scitools.idtdna.com/analyzer/oligocalc.asp. Other algorithms for calculating $T_m$ are known in the art and are optionally applied to the present invention.

Typically, the component of the label probe system (e.g., the amplification multimer or preamplifier) is capable of hybridizing simultaneously to two of the m label extenders in a subset, although it optionally hybridizes to three, four, or more of the label extenders. In one class of embodiments, e.g., embodiments in which two (or more) label extenders bind to the component of the label probe system, sequence L-2 is 20 nucleotides or less in length. For example, L-2 can be between 9 and 17 nucleotides in length, e.g., between 12 and 15 nucleotides in length, between 13 and 15 nucleotides in length, or between 13 and 14 nucleotides in length. As noted, m is at least two, and can be at least three, at least five, at least 10, or more. m can be the same or different from subset to subset of label extenders.

The label extenders can be configured in any of a variety of ways. For example, the two label extenders that hybridize to the component of the label probe system can assume a cruciform arrangement, with one label extender having L-1 5' of L-2 and the other label extender having L-1 3' of L-2. Unexpectedly, however, a configuration in which either the 5' or the 3' end of both label extenders hybridizes to the nucleic acid while the other end binds to the component yields stronger binding of the component to the nucleic acid than does a cruciform arrangement of the label extenders. Thus, in one class of embodiments, the at least two label extenders (e.g., the m label extenders in a subset) each have L-1 5' of L-2 or each have L-1 3' of L-2. For example, L-1, which hybridizes to the nucleic acid of interest, can be at the 5' end of each label extender, while L-2, which hybridizes to the component of the label probe system, is at the 3' end of each label extender (or vice versa). L-1 and L-2 are optionally separated by additional sequence. In one exemplary embodiment, L-1 is located at the 5' end of the label extender and is about 20-30 nucleotides in length, L-2 is located at the 3' end of the label extender and is about 13-14 nucleotides in length, and L-1 and L-2 are separated by a spacer (e.g., 5 Ts).

A label extender, preamplifier, amplification multimer, label probe, capture probe and/or capture extender optionally comprises at least one non-natural nucleotide. For example, a label extender and the component of the label probe system (e.g., the amplification multimer or preamplifier) optionally comprise, at complementary positions, at least one pair of non-natural nucleotides that base pair with each other but that do not Watson-Crick base pair with the bases typical to biological DNA or RNA (i.e., A, C, G, T, or U). Examples of nonnatural nucleotides include, but are not limited to, Locked NucleicAcid™ nucleotides (available from Exiqon A/S, (www.)exiqon.com; see, e.g., SantaLucia Jr. (1998) Proc Natl Acad Sci 95:1460-1465) and isoG, isoC, and other nucleotides used in the AEGIS system (Artificially Expanded Genetic Information System, available from EraGen Biosciences, (www.)eragen.com; see, e.g., U.S. Pat. No. 6,001,983, U.S. Pat. No. 6,037,120, and U.S. Pat. No. 6,140,496). Use of such non-natural base pairs (e.g., isoG-isoC base pairs) in the probes can, for example, reduce background and/or simplify probe design by decreasing cross hybridization, or it can permit use of shorter probes (e.g., shorter sequences L-2 and M-1) when the non-natural base pairs have higher binding affinities than do natural base pairs.

The methods can optionally be used to quantitate the amounts of the nucleic acids of interest present in the sample. For example, in one class of embodiments, an intensity of a signal from the label is measured, e.g., for each subset of particles or selected position on the solid support, and correlated with a quantity of the corresponding nucleic acid of interest present.

As noted, blocking probes are optionally also hybridized to the nucleic acids of interest, which can reduce background in the assay. For a given nucleic acid of interest, the corresponding label extenders, optional capture extenders, and optional blocking probes are preferably complementary to physically distinct, nonoverlapping sequences in the nucleic acid of interest, which are preferably, but not necessarily, contiguous. The $T_m$s of the capture extender-nucleic acid, label extender-nucleic acid, and blocking probe-nucleic acid complexes are preferably greater than the temperature at which the capture extenders, label extenders, and/or blocking probes are hybridized to the nucleic acid, e.g., by 5° C. or 10° C. or preferably by 15° C. or more, such that these complexes are stable at that temperature. Potential CE and LE sequences (e.g., potential sequences C-3 and L-1) are optionally examined for possible interactions with non-corresponding nucleic acids of interest, LEs or CEs, the preamplifier, the amplification multimer, the label probe, and/or any relevant genomic sequences, for example; sequences expected to cross-hybridize with undesired nucleic acids are typically not selected for use in the CEs or LEs. See, e.g., Player et al. (2001) "Single-copy gene detection using branched DNA (bDNA) in situ hybridization" J Histochem Cytochem 49:603-611 and U.S. patent application 60/680,976. Examination can be, e.g., visual (e.g., visual examination for complementarity), computational (e.g., computation and comparison of binding free energies), and/or experimental (e.g., cross-hybridization experiments). Capture probe sequences are preferably similarly examined, to ensure that the polynucleotide sequence C-1 complementary to a particular capture probe's sequence C-2 is not expected to cross-hybridize with any of the other capture probes that are to be associated with other subsets of particles or selected positions on the support.

At any of various steps, materials not captured on the solid support are optionally separated from the support. For example, after the capture extenders, nucleic acids, label extenders, blocking probes, and support-bound capture probes are hybridized, the support is optionally washed to remove unbound nucleic acids and probes; after the label extenders and amplification multimer are hybridized, the support is optionally washed to remove unbound amplification multimer; and/or after the label probes are hybridized to the amplification multimer, the support is optionally washed to remove unbound label probe prior to detection of the label.

In embodiments in which different nucleic acids are captured to different subsets of particles, one or more of the subsets of particles is optionally isolated, whereby the associated nucleic acid of interest is isolated. Similarly, nucleic acids can be isolated from selected positions on a spatially addressable solid support. The isolated nucleic acid can optionally be removed from the particles and/or subjected to further manipulation, if desired (e.g., amplification by PCR or the like).

The methods can be used to detect the presence of the nucleic acids of interest in essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids (e.g., DNA, RNA, mRNA, rRNA, miRNA, etc.). As just a few examples, the nucleic acids of interest can be derived from one or more of an animal, a human, a plant, a cultured cell, a microorganism, a virus, a bacterium, or a pathogen.

As noted, the methods can be used for gene expression analysis. Accordingly, in one class of embodiments, the two or more nucleic acids of interest comprise two or more mRNAs. The methods can also be used for clinical diagnosis and/or detection of microorganisms, e.g., pathogens. Thus, in certain embodiments, the nucleic acids include bacterial and/or viral genomic RNA and/or DNA (double-stranded or single-stranded), plasmid or other extra-genomic DNA, or other nucleic acids derived from microorganisms (pathogenic or otherwise). It will be evident that double-stranded nucleic acids of interest will typically be denatured before hybridization with capture extenders, label extenders, and the like.

An exemplary embodiment is schematically illustrated in FIG. 2. Panel A illustrates three distinguishable subsets of microspheres 201, 202, and 203, which have associated therewith capture probes 204, 205, and 206, respectively. Each capture probe includes a sequence C-2 (250), which is different from subset to subset of microspheres. The three subsets of microspheres are combined to form pooled population 208 (Panel B). A subset of capture extenders is provided for each nucleic acid of interest; subset 211 for nucleic acid 214, subset 212 for nucleic acid 215 which is not present, and subset 213 for nucleic acid 216. Each capture extender includes sequences C-1 (251, complementary to the respective capture probe's sequence C-2) and C-3 (252, complementary to a sequence in the corresponding nucleic acid of interest). Three subsets of label extenders (221, 222, and 223 for nucleic acids 214, 215, and 216, respectively) and three subsets of blocking probes (224, 225, and 226 for nucleic acids 214, 215, and 216, respectively) are also provided. Each label extender includes sequences L-1 (254, complementary to a sequence in the corresponding nucleic acid of interest) and L-2 (255, complementary to M-1). Non-target nucleic acids 230 are also present in the sample of nucleic acids.

Subsets of label extenders 221 and 223 are hybridized to nucleic acids 214 and 216, respectively. In addition, nucleic acids 214 and 216 are hybridized to their corresponding subset of capture extenders (211 and 213, respectively), and the capture extenders are hybridized to the corresponding capture probes (204 and 206, respectively), capturing nucleic acids 214 and 216 on microspheres 201 and 203, respectively (Panel C). Materials not bound to the microspheres (e.g., capture extenders 212, nucleic acids 230, etc.) are separated from the microspheres by washing. Label probe system 240 including preamplifier 245 (which includes two sequences M-1 257), amplification multimer 241 (which includes sequences M-2 258), and label probe 242 (which contains label 243) is provided. Each preamplifier 245 is hybridized to two label extenders, amplification multimers 241 are hybridized to the preamplifier, and label probes 242 are hybridized to the amplification multimers (Panel D). Materials not captured on the microspheres are optionally removed by washing the microspheres. Microspheres from each subset are identified, e.g., by their fluorescent emission spectrum ($\lambda_2$ and $\lambda_3$, Panel E), and the presence or absence of the label on each subset of microspheres is detected ($\lambda_1$, Panel E). Since each nucleic acid of interest is associated with a distinct subset of microspheres, the presence of the label on a given subset of microspheres correlates with the presence of the corresponding nucleic acid in the original sample.

As depicted in FIG. 2, all of the label extenders in all of the subsets typically include an identical sequence L-2. Optionally, however, different label extenders (e.g., label extenders in different subsets) can include different sequences L-2. Also as depicted in FIG. 2, each capture probe typically includes a single sequence C-2 and thus hybridizes to a single capture extender. Optionally, however, a capture probe can include two or more sequences C-2 and hybridize to two or more capture extenders. Similarly, as depicted, each of the capture extenders in a particular subset typically includes an identical sequence C-1, and thus only a single capture probe is needed for each subset of particles; however, different capture extenders within a subset optionally include different sequences C-1 (and thus hybridize to different sequences C-2, within a single capture probe or different capture probes on the surface of the corresponding subset of particles).

In the embodiment depicted in FIG. 2, the label probe system includes the preamplifier, amplification multimer, and label probe. It will be evident that similar considerations apply to embodiments in which the label probe system includes only an amplification multimer and label probe or only a label probe.

The various hybridization and capture steps can be performed simultaneously or sequentially, in any convenient order. For example, in embodiments in which capture extenders are employed, each nucleic acid of interest can be hybridized simultaneously with its corresponding subset of m label extenders and its corresponding subset of n capture extenders, and then the capture extenders can be hybridized with capture probes associated with the solid support. Materials not captured on the support are preferably removed, e.g., by washing the support, and then the label probe system is hybridized to the label extenders.

Figures 3A, 3B, 3C:
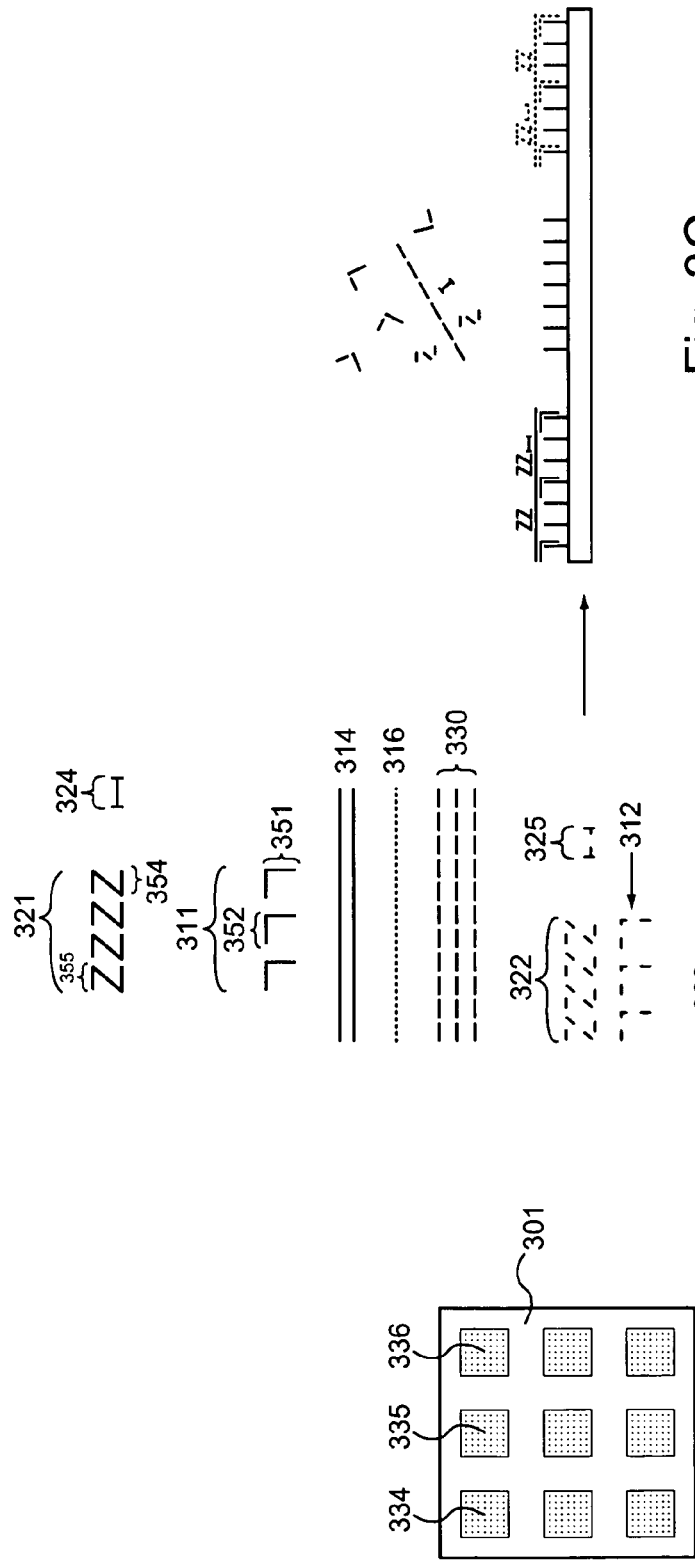
FIG. 3 Panels A-D schematically depict a multiplex nucleic acid detection assay, in which the nucleic acids of interest are captured at selected positions on a solid support and then detected. Panel A shows a top view of the solid support, while Panels B-D show the support in cross-section.
Figure 3D:
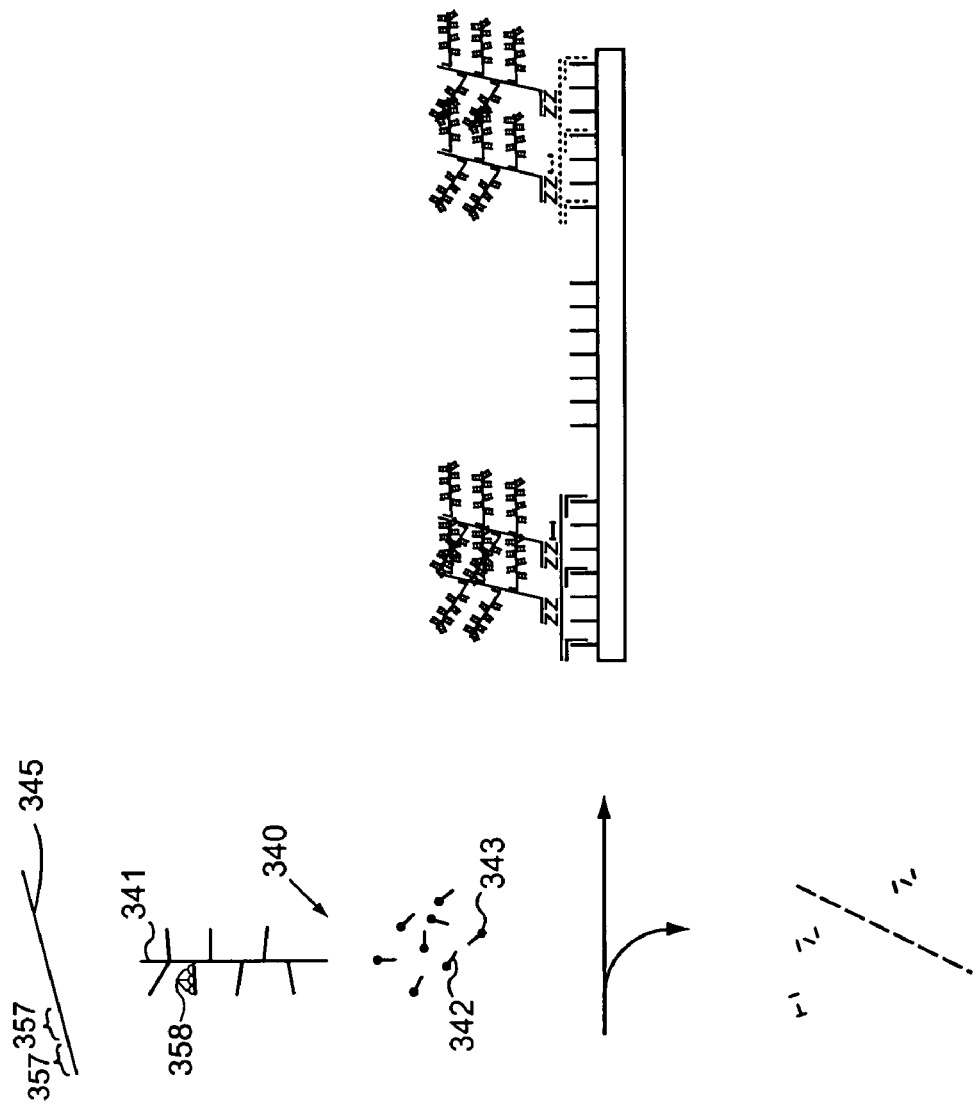

Another exemplary embodiment is schematically illustrated in FIG. 3. Panel A depicts solid support 301 having nine capture probes provided on it at nine selected positions (e.g., 334-336). Panel B depicts a cross section of solid support 301, with distinct capture probes 304, 305, and 306 at different selected positions on the support (334, 335, and 336, respectively). A subset of capture extenders is provided for each nucleic acid of interest. Only three subsets are depicted; subset 311 for nucleic acid 314, subset 312 for nucleic acid 315 which is not present, and subset 313 for nucleic acid 316. Each capture extender includes sequences C-1 (351, complementary to the respective capture probe's sequence C-2) and C-3 (352, complementary to a sequence in the corresponding nucleic acid of interest). Three subsets of label extenders (321, 322, and 323 for nucleic acids 314, 315, and 316, respectively) and three subsets of blocking probes (324, 325, and 326 for nucleic acids 314, 315, and 316, respectively) are also depicted (although nine would be provided, one for each nucleic acid of interest). Each label extender includes sequences L-1 (354, complementary to a sequence in the corresponding nucleic acid of interest) and L-2 (355, complementary to M-1). Non-target nucleic acids 330 are also present in the sample of nucleic acids.

Subsets of label extenders 321 and 323 are hybridized to nucleic acids 314 and 316, respectively. Nucleic acids 314 and 316 are hybridized to their corresponding subset of capture extenders (311 and 313, respectively), and the capture extenders are hybridized to the corresponding capture probes (304 and 306, respectively), capturing nucleic acids 314 and 316 at selected positions 334 and 336, respectively (Panel C). Materials not bound to the solid support (e.g., capture extenders 312, nucleic acids 330, etc.) are separated from the support by washing. Label probe system 340 including preamplifier 345 (which includes two sequences M-1 357), amplification multimer 341 (which includes sequences M-2 358) and label probe 342 (which contains label 343) is provided. Each preamplifier 345 is hybridized to two label extenders, amplification multimers 341 are hybridized to the preamplifier, and label probes 342 are hybridized to the amplification multimers (Panel D). Materials not captured on the solid support are optionally removed by washing the support, and the presence or absence of the label at each position on the solid support is detected. Since each nucleic acid of interest is associated with a distinct position on the support, the presence of the label at a given position on the support correlates with the presence of the corresponding nucleic acid in the original sample.

Another general class of embodiments provides methods of detecting one or more nucleic acids, using the novel label extender configuration described above. In the methods, a sample comprising or suspected of comprising the nucleic acids of interest, one or more subsets of m label extenders, wherein m is at least two, and a label probe system are provided. Each subset of m label extenders is capable of hybridizing to one of the nucleic acids of interest. The label probe system comprises a label, and a component of the label probe system (e.g., a preamplifier or an amplification multimer) is capable of hybridizing simultaneously to at least two of the m label extenders in a subset. Each label extender comprises a polynucleotide sequence L-1 that is complementary to a polynucleotide sequence in the corresponding nucleic acid of interest and a polynucleotide sequence L-2 that is complementary to a polynucleotide sequence in the component of the label probe system, and the at least two label extenders (e.g., the m label extenders in a subset) each have L-1 5' of L-2 or each have L-1 3' of L-2.

Those nucleic acids of interest present in the sample are captured on a solid support. Each nucleic acid of interest captured on the solid support is hybridized to its corresponding subset of m label extenders, and the label probe system (or the component thereof) is hybridized to the m label extenders at a hybridization temperature. The hybridization temperature is greater than a melting temperature $T_m$ of a complex between each individual label extender and the component of the label probe system. The presence or absence of the label on the solid support is then detected. Since the label is associated with the nucleic acid(s) of interest via hybridization of the label extenders and label probe system, the presence or absence of the label on the solid support is correlated with the presence or absence of the nucleic acid(s) of interest on the solid support and thus in the original sample.

Typically, the one or more nucleic acids of interest comprise two or more nucleic acids of interest, and the one or more subsets of m label extenders comprise two or more subsets of m label extenders.

The various hybridization and capture steps can be performed simultaneously or sequentially, in any convenient order. For example, in embodiments in which capture extenders are employed, each nucleic acid of interest can be hybridized simultaneously with its corresponding subset of m label extenders and its corresponding subset of n capture extenders, and then the capture extenders can be hybridized with capture probes associated with the solid support. Materials not captured on the support are preferably removed, e.g., by washing the support, and then the label probe system is hybridized to the label extenders.

As for the methods described above, essentially any suitable solid support can be employed. For example, the solid support can comprise particles such as microspheres, or it can comprise a substantially planar and/or spatially addressable support. Different nucleic acids are optionally captured on different distinguishable subsets of particles or at different positions on a spatially addressable solid support. The nucleic acids of interest can be captured to the solid support by any of a variety of techniques, for example, by binding directly to the solid support or by binding to a moiety bound to the support, or through hybridization to another nucleic acid bound to the solid support. Preferably, the nucleic acids are captured to the solid support through hybridization with capture extenders and capture probes.

In one class of embodiments in which the one or more nucleic acids of interest comprise two or more nucleic acids of interest and the one or more subsets of m label extenders comprise two or more subsets of m label extenders, a pooled population of particles which constitute the solid support is provided. The population comprises two or more subsets of particles, and a plurality of the particles in each subset is distinguishable from a plurality of the particles in every other subset. (Typically, substantially all of the particles in each subset are distinguishable from substantially all of the particles in every other subset.) The particles in each subset have associated therewith a different capture probe.

Two or more subsets of n capture extenders, wherein n is at least two, are also provided. Each subset of n capture extenders is capable of hybridizing to one of the nucleic acids of interest, and the capture extenders in each subset are capable of hybridizing to one of the capture probes, thereby associating each subset of n capture extenders with a selected subset of the particles. Each of the nucleic acids of interest present in the sample is hybridized to its corresponding subset of n capture extenders and the subset of n capture extenders is hybridized to its corresponding capture probe, thereby capturing the nucleic acid on the subset of particles with which the capture extenders are associated.

Typically, in this class of embodiments, at least a portion of the particles from each subset are identified and the presence or absence of the label on those particles is detected. Since a correlation exists between a particular subset of particles and a particular nucleic acid of interest, which subsets of particles have the label present indicates which of the nucleic acids of interest were present in the sample.

In other embodiments in which the one or more nucleic acids of interest comprise two or more nucleic acids of interest and the one or more subsets of m label extenders comprise two or more subsets of m label extenders, the nucleic acids are captured at different positions on a non-particulate, spatially addressable solid support. Thus, in one class of embodiments, the solid support comprises two or more capture probes, wherein each capture probe is provided at a selected position on the solid support. Two or more subsets of n capture extenders, wherein n is at least two, are provided. Each subset of n capture extenders is capable of hybridizing to one of the nucleic acids of interest, and the capture extenders in each subset are capable of hybridizing to one of the capture probes, thereby associating each subset of n capture extenders with a selected position on the solid support. Each of the nucleic acids of interest present in the sample is hybridized to its corresponding subset of n capture extenders and the subset of n capture extenders is hybridized to its corresponding capture probe, thereby capturing the nucleic acid on the solid support at the selected position with which the capture extenders are associated.

Typically, in this class of embodiments, the presence or absence of the label at the selected positions on the solid support is detected. Since a correlation exists between a particular position on the support and a particular nucleic acid of interest, which positions have a label present indicates which of the nucleic acids of interest were present in the sample.

Essentially all of the features noted for the methods above apply to these embodiments as well, as relevant; for example, with respect to composition of the label probe system; type of label; type of solid support; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

In one aspect, the invention provides methods for capturing a labeled probe to a target nucleic acid, through hybridization of the labeled probe directly to label extenders hybridized to the nucleic acid or through hybridization of the labeled probe to one or more nucleic acids that are in turn hybridized to the label extenders.

Accordingly, one general class of embodiments provides methods of capturing a label to a first nucleic acid of interest in a multiplex assay in which two or more nucleic acids of interest are to be detected. In the methods, a sample comprising the first nucleic acid of interest and also comprising or suspected of comprising one or more other nucleic acids of interest is provided. A first subset of m label extenders, wherein m is at least two, and a label probe system comprising the label are also provided. The first subset of m label extenders is capable of hybridizing to the first nucleic acid of interest, and a component of the label probe system is capable of hybridizing simultaneously to at least two of the m label extenders in the first subset. The first nucleic acid of interest is hybridized to the first subset of m label extenders, and the label probe system is hybridized to the m label extenders, thereby capturing the label to the first nucleic acid of interest.

Essentially all of the features noted for the embodiments above apply to these methods as well, as relevant; for example, with respect to configuration of the label extenders, number of label extenders per subset, composition of the label probe system, type of label, number of nucleic acids of interest, source of the sample and/or nucleic acids, and/or the like. For example, in one class of embodiments, the label probe system comprises a label probe, which label probe comprises the label, and which label probe is capable of hybridizing simultaneously to at least two of the m label extenders. In other embodiments, the label probe system includes the label probe and an amplification multimer that is capable of hybridizing simultaneously to at least two of the m label extenders. Similarly, in yet other embodiments, the label probe system includes the label probe, an amplification multimer, and a preamplifier that is capable of hybridizing simultaneously to at least two of the m label extenders.

Another general class of embodiments provides methods of capturing a label to a nucleic acid of interest. In the methods, m label extenders, wherein m is at least two, are provided. The m label extenders are capable of hybridizing to the nucleic acid of interest. A label probe system comprising the label is also provided. A component of the label probe system is capable of hybridizing simultaneously to at least two of the m label extenders. Each label extender comprises a polynucleotide sequence L-1 that is complementary to a polynucleotide sequence in the nucleic acid of interest and a polynucleotide sequence L-2 that is complementary to a polynucleotide sequence in the component of the label probe system, and the m label extenders each have L-1 5' of L-2 or wherein the m label extenders each have L-1 3' of L-2. The nucleic acid of interest is hybridized to the m label extenders, and the label probe system is hybridized to the m label extenders at a hybridization temperature, thereby capturing the label to the nucleic acid of interest. Preferably, the hybridization temperature is greater than a melting temperature $T_m$ of a complex between each individual label extender and the component of the label probe system.

Essentially all of the features noted for the embodiments above apply to these methods as well, as relevant; for example, with respect to configuration of the label extenders, number of label extenders per subset, composition of the label probe system, type of label, and/or the like. For example, in one class of embodiments, the label probe system comprises a label probe, which label probe comprises the label, and which label probe is capable of hybridizing simultaneously to at least two of the m label extenders. In other embodiments, the label probe system includes the label probe and an amplification multimer that is capable of hybridizing simultaneously to at least two of the m label extenders. Similarly, in yet other embodiments, the label probe system includes the label probe, an amplification multimer, and a preamplifier that is capable of hybridizing simultaneously to at least two of the m label extenders.

Compositions

Compositions related to the methods are another feature of the invention. Thus, one general class of embodiments provides a composition for detecting two or more nucleic acids of interest. In one aspect, the composition includes a pooled population of particles. The population comprises two or more subsets of particles, with a plurality of the particles in each subset being distinguishable from a plurality of the particles in every other subset. The particles in each subset have associated therewith a different capture probe. In another aspect, the composition includes a solid support comprising two or more capture probes, wherein each capture probe is provided at a selected position on the solid support.

The composition also includes two or more subsets of n capture extenders, wherein n is at least two, two or more subsets of m label extenders, wherein m is at least two, and a label probe system comprising a label, wherein a component of the label probe system is capable of hybridizing simultaneously to at least two of the m label extenders in a subset. Each subset of n capture extenders is capable of hybridizing to one of the nucleic acids of interest, and the capture extenders in each subset are capable of hybridizing to one of the capture probes and thereby associating each subset of n capture extenders with a selected subset of the particles or with a selected position on the solid support. Similarly, each subset of m label extenders is capable of hybridizing to one of the nucleic acids of interest.

The composition optionally includes a sample comprising or suspected of comprising at least one of the nucleic acids of interest, e.g., two or more, three or more, etc. nucleic acids. Optionally, the composition comprises one or more of the nucleic acids of interest. In one class of embodiments, each nucleic acid of interest present in the composition is hybridized to its corresponding subset of n capture extenders, and the corresponding subset of n capture extenders is hybridized to its corresponding capture probe. Each nucleic acid of interest is thus associated with an identifiable subset of the particles. In this class of embodiments, each nucleic acid of interest present in the composition is also hybridized to its corresponding subset of m label extenders. The component of the label probe system (e.g., the amplification multimer or preamplifier) is hybridized to the m label extenders. The composition is maintained at a hybridization temperature that is greater than a melting temperature $T_m$ of a complex between each individual label extender and the component of the label probe system (e.g., the amplification multimer or preamplifier). The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Essentially all of the features noted for the methods above apply to these embodiments as well, as relevant; for example, with respect to composition of the label probe system; type of label; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

Another general class of embodiments provides a composition for detecting one or more nucleic acids of interest. The composition includes a solid support comprising one or more capture probes, one or more subsets of n capture extenders, wherein n is at least two, one or more subsets of m label extenders, wherein m is at least two, and a label probe system comprising a label. Each subset of n capture extenders is capable of hybridizing to one of the nucleic acids of interest, and the capture extenders in each subset are capable of hybridizing to one of the capture probes and thereby associating each subset of n capture extenders with the solid support. Each subset of m label extenders is capable of hybridizing to one of the nucleic acids of interest. A component of the label probe system (e.g., a preamplifier or amplification multimer) is capable of hybridizing simultaneously to at least two of the m label extenders in a subset. Each label extender comprises a polynucleotide sequence L-1 that is complementary to a polynucleotide sequence in the corresponding nucleic acid of interest and a polynucleotide sequence L-2 that is complementary to a polynucleotide sequence in the component of the label probe system, and the at least two label extenders (e.g., the m label extenders in a subset) each have L-1 5' of L-2 or each have L-1 3' of L-2.

In one class of embodiments, the one or more nucleic acids of interest comprise two or more nucleic acids of interest, the one or more subsets of n capture extenders comprise two or more subsets of n capture extenders, the one or more subsets of m label extenders comprise two or more subsets of m label extenders, and the solid support comprises a pooled population of particles. The population comprises two or more subsets of particles. A plurality of the particles in each subset are distinguishable from a plurality of the particles in every other subset, and the particles in each subset have associated therewith a different capture probe. The capture extenders in each subset are capable of hybridizing to one of the capture probes and thereby associating each subset of n capture extenders with a selected subset of the particles.

In another class of embodiments, the one or more nucleic acids of interest comprise two or more nucleic acids of interest, the one or more subsets of n capture extenders comprise two or more subsets of n capture extenders, the one or more subsets of m label extenders comprise two or more subsets of m label extenders, and the solid support comprises two or more capture probes, wherein each capture probe is provided at a selected position on the solid support. The capture extenders in each subset are capable of hybridizing to one of the capture probes and thereby associating each subset of n capture extenders with a selected position on the solid support.

Essentially all of the features noted for the embodiments above apply to these embodiments as well, as relevant; for example, with respect to composition of the label probe system; type of label; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

For example, the label probe system can include an amplification multimer or preamplifier, which amplification multimer or preamplifier is capable of hybridizing to the at least two label extenders. The composition optionally includes one or more of the nucleic acids of interest, wherein each nucleic acid of interest is hybridized to its corresponding subset of m label extenders and to its corresponding subset of n capture extenders, which in turn is hybridized to its corresponding capture probe. The amplification multimer or preamplifier is hybridized to the m label extenders. The composition is maintained at a hybridization temperature that is greater than a melting temperature $T_m$ of a complex between each individual label extender and the amplification multimer or preamplifier (e.g., about 5° C. or more, about 7° C. or more, about 10° C. or more, about 12° C. or more, about 15° C. or more, about 17° C. or more, or about 20° C. or more greater than the $T_m$).

Kits

Yet another general class of embodiments provides a kit for detecting two or more nucleic acids of interest. In one aspect, the kit includes a pooled population of particles. The population comprises two or more subsets of particles, with a plurality of the particles in each subset being distinguishable from a plurality of the particles in every other subset. The particles in each subset have associated therewith a different capture probe. In another aspect, the kit includes a solid support comprising two or more capture probes, wherein each capture probe is provided at a selected position on the solid support.

The kit also includes two or more subsets of n capture extenders, wherein n is at least two, two or more subsets of m label extenders, wherein m is at least two, and a label probe system comprising a label, wherein a component of the label probe system is capable of hybridizing simultaneously to at least two of the m label extenders in a subset. Each subset of n capture extenders is capable of hybridizing to one of the nucleic acids of interest, and the capture extenders in each subset are capable of hybridizing to one of the capture probes and thereby associating each subset of n capture extenders with a selected subset of the particles or with a selected position on the solid support. Similarly, each subset of m label extenders is capable of hybridizing to one of the nucleic acids of interest. The components of the kit are packaged in one or more containers. The kit optionally also includes instructions for using the kit to capture and detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to composition of the label probe system; type of label; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

Another general class of embodiments provides a kit for detecting one or more nucleic acids of interest. The kit includes a solid support comprising one or more capture probes, one or more subsets of n capture extenders, wherein n is at least two, one or more subsets of m label extenders, wherein m is at least two, and a label probe system comprising a label. Each subset of n capture extenders is capable of hybridizing to one of the nucleic acids of interest, and the capture extenders in each subset are capable of hybridizing to one of the capture probes and thereby associating each subset of n capture extenders with the solid support. Each subset of m label extenders is capable of hybridizing to one of the nucleic acids of interest. A component of the label probe system (e.g., a preamplifier or amplification multimer) is capable of hybridizing simultaneously to at least two of the m label extenders in a subset. Each label extender comprises a polynucleotide sequence L-1 that is complementary to a polynucleotide sequence in the corresponding nucleic acid of interest and a polynucleotide sequence L-2 that is complementary to a polynucleotide sequence in the component of the label probe system, and the at least two label extenders (e.g., the m label extenders in a subset) each have L-1 5' of L-2 or each have L-1 3' of L-2. The components of the kit are packaged in one or more containers. The kit optionally also includes instructions for using the kit to capture and detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to composition of the label probe system; type of label; inclusion of blocking probes; configuration of the capture extenders, capture probes, label extenders, and/or blocking probes; number of nucleic acids of interest and of subsets of particles or selected positions on the solid support, capture extenders and label extenders; number of capture or label extenders per subset; type of particles; source of the sample and/or nucleic acids; and/or the like.

For example, in one class of embodiments, the one or more nucleic acids of interest comprise two or more nucleic acids of interest, the one or more subsets of n capture extenders comprise two or more subsets of n capture extenders, the one or more subsets of m label extenders comprise two or more subsets of m label extenders, and the solid support comprises a pooled population of particles. The population comprises two or more subsets of particles. A plurality of the particles in each subset are distinguishable from a plurality of the particles in every other subset, and the particles in each subset have associated therewith a different capture probe. The capture extenders in each subset are capable of hybridizing to one of the capture probes and thereby associating each subset of n capture extenders with a selected subset of the particles.

In another class of embodiments, the one or more nucleic acids of interest comprise two or more nucleic acids of interest, the one or more subsets of n capture extenders comprise two or more subsets of n capture extenders, the one or more subsets of m label extenders comprise two or more subsets of m label extenders, and the solid support comprises two or more capture probes, wherein each capture probe is provided at a selected position on the solid support. The capture extenders in each subset are capable of hybridizing to one of the capture probes and thereby associating each subset of n capture extenders with a selected position on the solid support.

Systems

In one aspect, the invention includes systems, e.g., systems used to practice the methods herein and/or comprising the compositions described herein. The system can include, e.g., a fluid and/or microsphere handling element, a fluid and/or microsphere containing element, a laser for exciting a fluorescent label and/or fluorescent microspheres, a detector for detecting light emissions from a chemiluminescent reaction or fluorescent emissions from a fluorescent label and/or fluorescent microspheres, and/or a robotic element that moves other components of the system from place to place as needed (e.g., a multiwell plate handling element). For example, in one class of embodiments, a composition of the invention is contained in a flow cytometer, a Luminex 100™ or HTS™ instrument, a microplate reader, a microarray reader, a luminometer, a calorimeter, or like instrument.

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or laser). The computer can also receive data from other components of the system, e.g., from a detector, and can interpret the data, provide it to a user in a human readable format, or use that data to initiate further operations, in accordance with any programming by the user.

Labels

A wide variety of labels are well known in the art and can be adapted to the practice of the present invention. For example, luminescent labels and light-scattering labels (e.g., colloidal gold particles) have been described. See, e.g., Csaki et al. (2002) "Gold nanoparticles as novel label for DNA diagnostics" Expert Rev Mol Diagn 2:187-93.

As another example, a number of fluorescent labels are well known in the art, including but not limited to, hydrophobic fluorophores (e.g., phycoerythrin, rhodamine, Alexa Fluor 488 and fluorescein), green fluorescent protein (GFP) and variants thereof (e.g., cyan fluorescent protein and yellow fluorescent protein), and quantum dots. See e.g., The Handbook: A Guide to Fluorescent Probes and Labeling Technologies, Tenth Edition or Web Edition (2006) from Invitrogen (available on the world wide web at probes.invitrogen.com/handbook), for descriptions of fluorophores emitting at various different wavelengths (including tandem conjugates of fluorophores that can facilitate simultaneous excitation and detection of multiple labeled species). For use of quantum dots as labels for biomolecules, see e.g., Dubertret et al. (2002) Science 298:1759; Nature Biotechnology (2003) 21:41-46; and Nature Biotechnology (2003) 21:47-51.

Labels can be introduced to molecules, e.g. polynucleotides, during synthesis or by postsynthetic reactions by techniques established in the art; for example, kits for fluorescently labeling polynucleotides with various fluorophores are available from Molecular Probes, Inc. ((www.)molecularprobes.com), and fluorophore-containing phosphoramidites for use in nucleic acid synthesis are commercially available. Similarly, signals from the labels (e.g., absorption by and/or fluorescent emission from a fluorescent label) can be detected by essentially any method known in the art. For example, multicolor detection, detection of FRET, fluorescence polarization, and the like, are well known in the art.

Microspheres

Microspheres are preferred particles in certain embodiments described herein since they are generally stable, are widely available in a range of materials, surface chemistries and uniform sizes, and can be fluorescently dyed. Microspheres can be distinguished from each other by identifying characteristics such as their size (diameter) and/or their fluorescent emission spectra, for example.

Luminex Corporation ((www.)luminexcorp.com), for example, offers 100 sets of uniform diameter polystyrene microspheres. The microspheres of each set are internally labeled with a distinct ratio of two fluorophores. A flow cytometer or other suitable instrument can thus be used to classify each individual microsphere according to its predefined fluorescent emission ratio. Fluorescently-coded microsphere sets are also available from a number of other suppliers, including Radix Biosolutions ((www.)radixbiosolutions.com) and Upstate Biotechnology ((www.)upstatebiotech.com). Alternatively, BD Biosciences ((www.)bd.com) and Bangs Laboratories, Inc. ((www.)bangslabs.com) offer microsphere sets distinguishable by a combination of fluorescence and size. As another example, microspheres can be distinguished on the basis of size alone, but fewer sets of such microspheres can be multiplexed in an assay because aggregates of smaller microspheres can be difficult to distinguish from larger microspheres.

Microspheres with a variety of surface chemistries are commercially available, from the above suppliers and others (e.g., see additional suppliers listed in Kellar and Iannone (2002) "Multiplexed microsphere-based flow cytometric assays" Experimental Hematology 30:1227-1237 and Fitzgerald (2001) "Assays by the score" The Scientist 15[11]: 25). For example, microspheres with carboxyl, hydrazide or maleimide groups are available and permit covalent coupling of molecules (e.g., polynucleotide capture probes with free amine, carboxyl, aldehyde, sulfhydryl or other reactive groups) to the microspheres. As another example, microspheres with surface avidin or streptavidin are available and can bind biotinylated capture probes; similarly, microspheres coated with biotin are available for binding capture probes conjugated to avidin or streptavidin. In addition, services that couple a capture reagent of the customer's choice to microspheres are commercially available, e.g., from Radix Biosolutions ((www.)radixbiosolutions.com).

Protocols for using such commercially available microspheres (e.g., methods of covalently coupling polynucleotides to carboxylated microspheres for use as capture probes, methods of blocking reactive sites on the microsphere surface that are not occupied by the polynucleotides, methods of binding biotinylated polynucleotides to avidin-functionalized microspheres, and the like) are typically supplied with the microspheres and are readily utilized and/or adapted by one of skill. In addition, coupling of reagents to microspheres is well described in the literature. For example, see Yang et al. (2001) "BADGE, Beads Array for the Detection of Gene Expression, a high-throughput diagnostic bioassay" Genome Res. 11:1888-98; Fulton et al. (1997) "Advanced multiplexed analysis with the FlowMetrix™ system" Clinical Chemistry 43:1749-1756; Jones et al. (2002) "Multiplex assay for detection of strain-specific antibodies against the two variable regions of the G protein of respiratory syncytial virus" 9:633-638; Camilla et al. (2001) "Flow cytometric microsphere-based immunoassay: Analysis of secreted cytokines in whole-blood samples from asthmatics" Clinical and Diagnostic Laboratory Immunology 8:776-784; Martins (2002) "Development of internal controls for the Luminex instrument as part of a multiplexed seven-analyte viral respiratory antibody profile" Clinical and Diagnostic Laboratory Immunology 9:41-45; Kellar and Iannone (2002) "Multiplexed microsphere-based flow cytometric assays" Experimental Hematology 30:1227-1237; Oliver et al. (1998) "Multiplexed analysis of human cytokines by use of the FlowMetrix system" Clinical Chemistry 44:2057-2060; Gordon and McDade (1997) "Multiplexed quantification of human IgG, IgA, and IgM with the FlowMetrix™ system" Clinical Chemistry 43:1799-1801; U.S. Pat. No. 5,981,180 entitled "Multiplexed analysis of clinical specimens apparatus and methods" to Chandler et al. (Nov. 9, 1999); U.S. Pat. No. 6,449,562 entitled "Multiplexed analysis of clinical specimens apparatus and methods" to Chandler et al. (Sep. 10, 2002); and references therein.

Methods of analyzing microsphere populations (e.g. methods of identifying microsphere subsets by their size and/or fluorescence characteristics, methods of using size to distinguish microsphere aggregates from single uniformly sized microspheres and eliminate aggregates from the analysis, methods of detecting the presence or absence of a fluorescent label on the microsphere subset, and the like) are also well described in the literature. See, e.g., the above references.

Suitable instruments, software, and the like for analyzing microsphere populations to distinguish subsets of microspheres and to detect the presence or absence of a label (e.g., a fluorescently labeled label probe) on each subset are commercially available. For example, flow cytometers are widely available, e.g., from Becton-Dickinson ((www.)bd.com) and Beckman Coulter ((www.)beckman.com). Luminex 100™ and Luminex HTS™ systems (which use microfluidics to align the microspheres and two lasers to excite the microspheres and the label) are available from Luminex Corporation ((www.)luminexcorp.com); the similar Bio-Plex™ Protein Array System is available from Bio-Rad Laboratories, Inc. ((www.)bio-rad.com). A confocal microplate reader suitable for microsphere analysis, the FMAT™ System 8100, is available from Applied Biosystems ((www.)appliedbiosystems.com).

As another example of particles that can be adapted for use in the present invention, sets of microbeads that include optical barcodes are available from CyVera Corporation ((www.)cyvera.com). The optical barcodes are holographically inscribed digital codes that diffract a laser beam incident on the particles, producing an optical signature unique for each set of microbeads.

Molecular Biological Techniques

In practicing the present invention, many conventional techniques in molecular biology, microbiology, and recombinant DNA technology are optionally used. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., Current Protocols, a joint venture between Greene Publishing Associates, Inc. and John Wiley & Sons, Inc., (supplemented through 2006). Other useful references, e.g. for cell isolation and culture (e.g., for subsequent nucleic acid or protein isolation) include Freshney (1994) Culture of Animal Cells, a Manual of Basic Technique, third edition, Wiley-Liss, N.Y. and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla.

Making Polynucleotides

Methods of making nucleic acids (e.g., by in vitro amplification, purification from cells, or chemical synthesis), methods for manipulating nucleic acids (e.g., by restriction enzyme digestion, ligation, etc.) and various vectors, cell lines and the like useful in manipulating and making nucleic acids are described in the above references. In addition, methods of making branched polynucleotides (e.g., amplification multimers) are described in U.S. Pat. No. 5,635,352, U.S. Pat. No. 5,124,246, U.S. Pat. No. 5,710,264, and U.S. Pat. No. 5,849,481, as well as in other references mentioned above.

In addition, essentially any polynucleotide (including, e.g., labeled or biotinylated polynucleotides) can be custom or standard ordered from any of a variety of commercial sources, such as The Midland Certified Reagent Company ((www.) mcrc.com), The Great American Gene Company ((www.) genco.com), ExpressGen Inc. ((www.)expressgen.com), Qiagen (oligos.qiagen.com) and many others.

A label, biotin, or other moiety can optionally be introduced to a polynucleotide, either during or after synthesis. For example, a biotin phosphoramidite can be incorporated during chemical synthesis of a polynucleotide. Alternatively, any nucleic acid can be biotinylated using techniques known in the art; suitable reagents are commercially available, e.g., from Pierce Biotechnology ((www.)piercenet.com). Similarly, any nucleic acid can be fluorescently labeled, for example, by using commercially available kits such as those from Molecular Probes, Inc. ((www.)molecularprobes.com) or Pierce Biotechnology ((www.)piercenet.com) or by incorporating a fluorescently labeled phosphoramidite during chemical synthesis of a polynucleotide.

Arrays

In an array of capture probes on a solid support (e.g., a membrane, a glass or plastic slide, a silicon or quartz chip, a plate, or other spatially addressable solid support), each capture probe is typically bound (e.g., electrostatically or covalently bound, directly or via a linker) to the support at a unique selected location. Methods of making, using, and analyzing such arrays (e.g., microarrays) are well known in the art. See, e.g., Baldi et al. (2002) DNA Microarrays and Gene Expression: From Experiments to Data Analysis and Modeling, Cambridge University Press; Beaucage (2001) "Strategies in the preparation of DNA oligonucleotide arrays for diagnostic applications" Curr Med Chem 8:1213-1244; Schena, ed. (2000) Microarray Biochip Technology, pp. 19-38, Eaton Publishing; technical note "Agilent SurePrint Technology: Content centered microarray design enabling speed and flexibility" available on the web at chem.agilent-.com/temp/rad01539/00039489.pdf; and references therein. Arrays of pre-synthesized polynucleotides can be formed (e.g., printed), for example, using commercially available instruments such as a GMS 417 Arrayer (Affymetrix, Santa Clara, Calif.). Alternatively, the polynucleotides can be synthesized at the selected positions on the solid support; see, e.g., U.S. Pat. No. 6,852,490 and U.S. Pat. No. 6,306,643, each to Gentanlen and Chee entitled "Methods of using an array of pooled probes in genetic analysis."

Suitable solid supports are commercially readily available. For example, a variety of membranes (e.g., nylon, PVDF, and nitrocellulose membranes) are commercially available, e.g., from Sigma-Aldrich, Inc. ((www.)sigmaaldrich.com). As another example, surface-modified and pre-coated slides with a variety of surface chemistries are commercially available, e.g., from TeleChem International ((www.)arrayit.com), Corning, Inc. (Corning, N.Y.), or Greiner Bio-One, Inc. ((www.)greinerbiooneinc.com). For example, silanated and silyated slides with free amino and aldehyde groups, respectively, are available and permit covalent coupling of molecules (e.g., polynucleotides with free aldehyde, amine, or other reactive groups) to the slides. As another example, slides with surface streptavidin are available and can bind biotinylated capture probes. In addition, services that produce arrays of polynucleotides of the customer's choice are commercially available, e.g., from TeleChem International ((www.)arrayit.com) and Agilent Technologies (Palo Alto, Calif.).

Suitable instruments, software, and the like for analyzing arrays to distinguish selected positions on the solid support and to detect the presence or absence of a label (e.g., a fluorescently labeled label probe) at each position are commercially available. For example, microarray readers are available, e.g., from Agilent Technologies (Palo Alto, Calif.), Affymetrix (Santa Clara, Calif.), and Zeptosens (Switzerland).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

The following sets forth a series of experiments that illustrate label extender design and that demonstrate that a configuration in which the 5' ends of the label extenders hybridize to a nucleic acid of interest while the 3' ends of the label extenders hybridize to a preamplifier results in stronger binding of the preamplifier to the nucleic acid than does a cruciform arrangement of the label extenders.

Figure 4B:
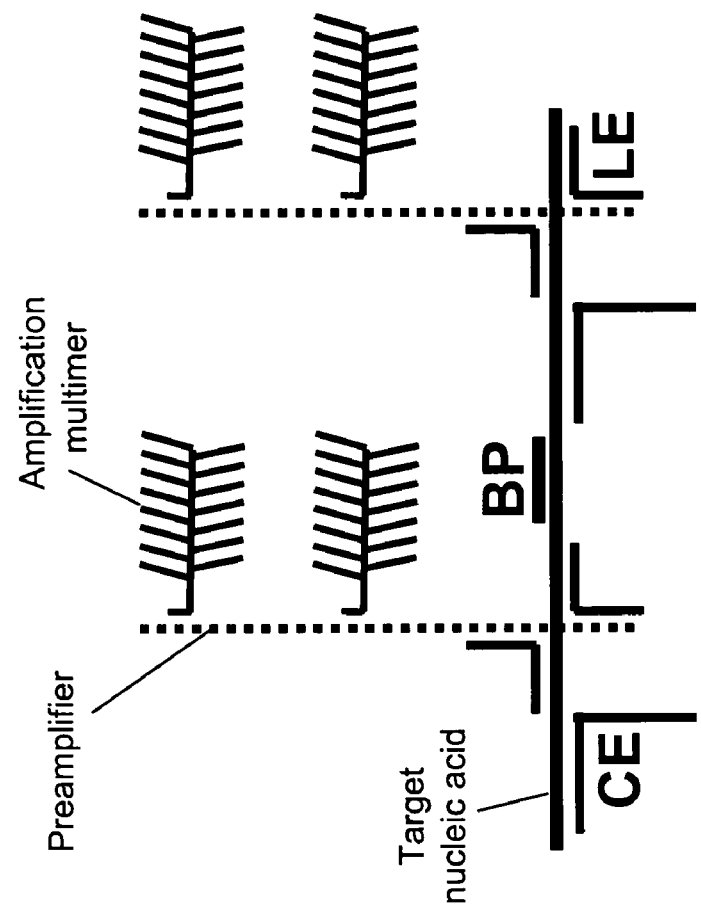
FIG. 4 Panel A schematically depicts a double Z label extender configuration. Panel B schematically depicts a cruciform label extender configuration. Panel C depicts a bar graph comparing luminescence observed in bDNA assays using double Z configuration label extenders or cruciform label extenders.
Figure 4A:
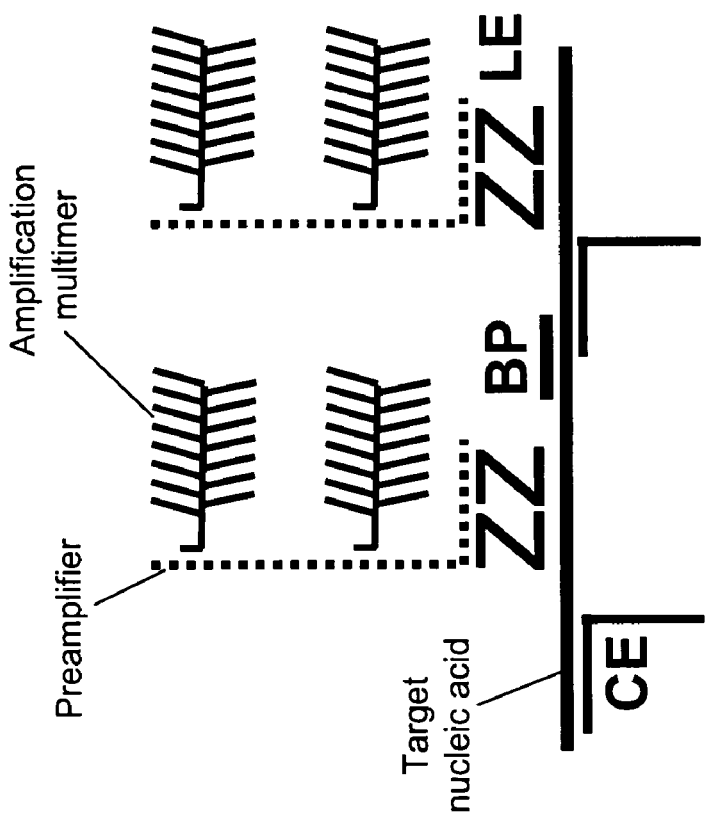
Figure 4C:
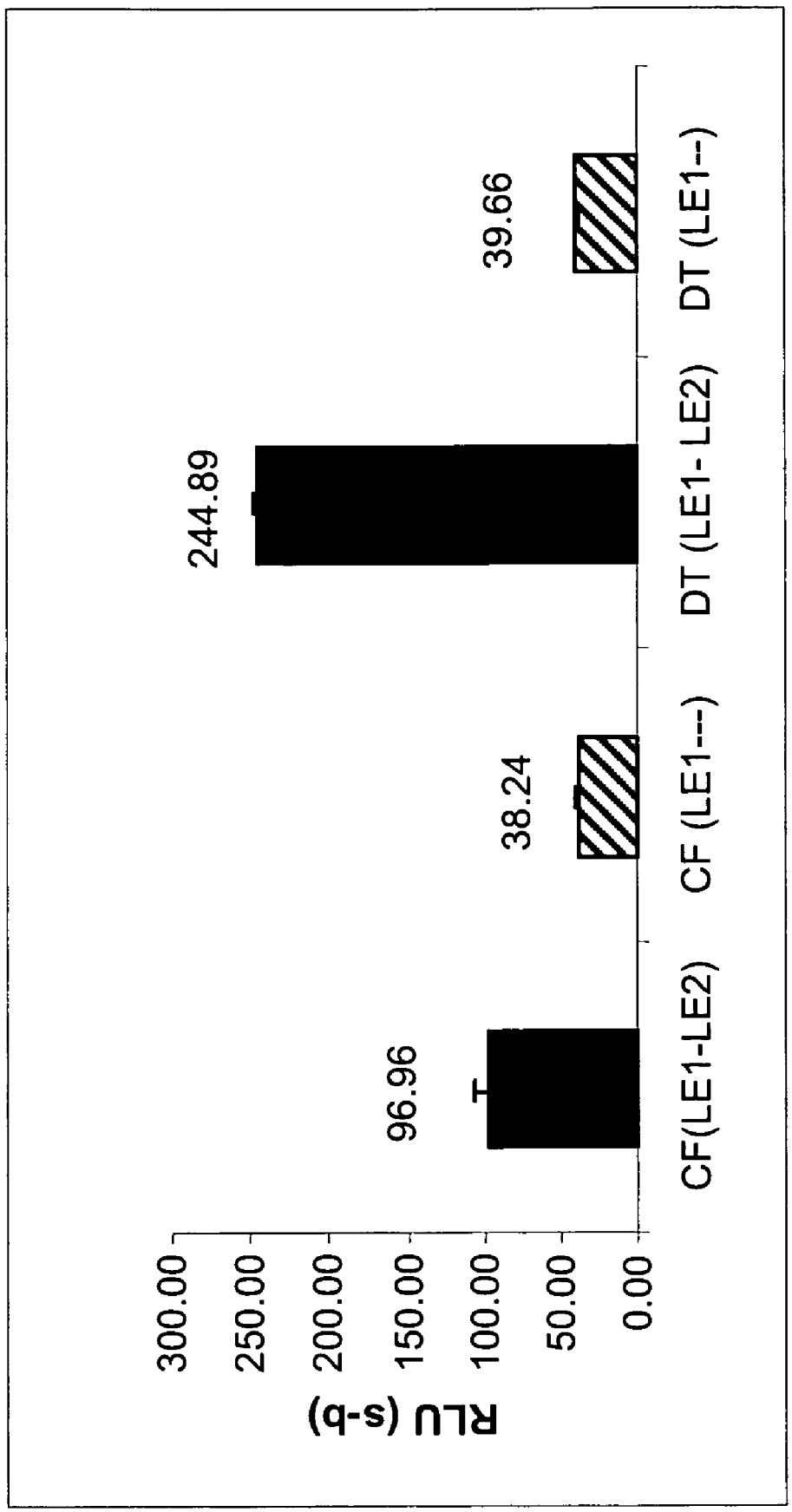

Two subsets of label extenders were designed to bind to a human GAPD nucleic acid target and to a preamplifier, as schematically illustrated in FIG. 4. Two label extenders bind each copy of the preamplifier. As shown in Panel A, in one subset of label extenders, the two label extenders in each pair bind the preamplifier through the same end (the 5' end, in this example) and bind the target nucleic acid through the other end (double Z configuration). As shown in Panel B, in the other subset of label extenders, the two label extenders in each pair bind the preamplifier through opposite ends: the 5' end of one label extender hybridizes to the preamplifier and the 3' end to the target, while the 3' end of the other label extender hybridizes to the preamplifier and the 5' end to the target (cruciform configuration). Sequence L-2 (complementary to the preamplifier) is 14 nucleotides in length for each label extender, and comparable sequences L-2 and L-1 were used for the corresponding label extenders in both configurations. Sequences of the label extenders are presented in Tables 1 and 2. The sequence of the preamplifier is 5' AGGCATAGGAC-CCGTGTCT tttttttt AGGCATAGGACCCGTGTCT ttttt ATGCTTTGACTCAG AAAACGGTAACTTC 3' (SEQ ID NO: 1); the underlined sequences are complementary to sequences in the label extenders.

TABLE 1

Label extenders for the cruciform configuration. In each label extender, sequence L-2 (complementary to a sequence in the preamplifier) is underlined.

| GAPD127 | ccagtggactccacgacgtacTTTT Tgaagttaccgtttt | CP1 tail | SEQ ID NO:2 |
| GAPD128 | ctgagtcaaagcatTTTTTttctcc atggtggtgaagacg | CP2 head | SEQ ID NO:3 |
| GAPD129 | tcttgaggctgttgtcatacttctT TTTTgaagttaccgtttt | CP1 tail | SEQ ID NO:4 |
| GAPD130 | ctgagtcaaagcatTTTTTgcagga ggcattgctgatga | CP2 head | SEQ ID NO:5 |
| GAPD131 | cagtagaggcagggatgatgttcTT TTTgaagttaccgtttt | CP1 tail | SEQ ID NO:6 |
| GAPD132 | ctgagtcaaagcatTTTTTcacagc cttggcagcgc | CP2 head | SEQ ID NO:7 |

TABLE 2

Label extenders for the double Z configuration. In each label extender, sequence L-2 (complementary to a sequence in the preamplifier) is underlined.

| | | | |
|---|---|---|---|
| GAPD217 | ccagtggactccacgacgtacTTT<br>TT<u>gaagttaccgtttt</u> | CP1<br>tail | SEQ ID NO:8 |
| GAPD218 | ttctccatggtggtgaagacgTTT<br>TT<u>ctgagtcaaagcat</u> | CP2<br>tail | SEQ ID NO:9 |
| GAPD219 | tcttgaggctgttgtcatacttct<br>TTTTT<u>gaagttaccgtttt</u> | CP1<br>tail | SEQ ID NO:10 |
| GAPD220 | gcaggaggcattgctgatgaTTTT<br>T<u>ctgagtcaaagcat</u> | CP2<br>tail | SEQ ID NO:11 |
| GAPD221 | cagtagaggcagggatgatgttcT<br>TTT<u>gaagttaccgtttt</u> | CP1<br>tail | SEQ ID NO:12 |
| GAPD222 | cacagccttggcagcgcTTTTT<u>ct<br>gagtcaaagcat</u> | CP2<br>tail | SEQ ID NO:13 |

The double Z and cruciform label extender configurations were assessed in single plex QuantiGene™ bDNA assays using essentially standard QuantiGene™ assay conditions. QuantiGene™ kits are commercially available from Panomics, Inc. (on the world wide web at (www.)panomics.com). Assays were performed basically as described in the supplier's instructions, with incubation at 53° C. on day one and 46° C. on day two, 1×GAPD probe set, 10 amole/well of GAPD in vitro transcribed RNA, preamplifier concentration of 100 fmol/well with incubation for one hour at 46° C., amplification multimer (1.0 amp, Bayer) at 100 fmol/well with incubation for one hour at 46° C., followed by label probe at 100 fmol/well (1:1000 dilution) for one hour at 46° C., then substrate for 30 minutes at 46° C. In this experiment, the only difference between the two assays is whether the cruciform configuration label extender set or the double Z configuration label extender set is used.

The results are illustrated in FIG. 4 Panel C, which shows background-subtracted luminescence (Relative Light Units, signal minus background) measured for the cruciform configuration and the double Z configuration label extenders. The signal for the assay using the double Z configuration label extenders (DT LE1-LE2) is almost 2.5 fold higher than that for the assay using the cruciform configuration label extenders (CF LE1-LE2). For comparison, assays in which only one label extender from each pair was included in the assay gave similar signals regardless of whether the single label extender binding to the preamplifier was from the cruciform (CF LE1-) or the double Z (DT LE1-)subset.

The stronger signal observed using the double Z configuration label extenders demonstrates that this design enables more efficient capture of the preamplifier than does the cruciform design.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of detecting one or more nucleic acids of interest, the method comprising:
   a) providing a sample comprising or suspected of comprising the one or more nucleic acids of interest;
   b) capturing those nucleic acids of interest present in the sample on a solid support;
   c) providing one or more subsets of m label extenders, wherein m is at least two, wherein each subset of m label extenders is capable of hybridizing to one of the nucleic acids of interest;
   d) providing a label probe system comprising a label, wherein a component of the label probe system is capable of hybridizing simultaneously to at least two of the m label extenders in a subset, wherein each of said at least two label extenders comprises a polynucleotide sequence L-1 that is complementary to a polynucleotide sequence in the corresponding nucleic acid of interest and comprises a polynucleotide sequence L-2 that is complementary to a polynucleotide sequence in the component of the label probe system, wherein said at least two label extenders all have L-1 5' of L-2 or all have L-1 3' of L-2, and wherein the m label extenders in the subset are complementary to nonoverlapping sequences in the corresponding nucleic acid of interest;
   e) hybridizing any nucleic acid of interest captured on the solid support to its corresponding subset of m label extenders;
   f) hybridizing the label probe system to the m label extenders at a hybridization temperature, which hybridization temperature is greater than a melting temperature $T_m$ of a complex between each individual label extender and the component of the label probe system; and
   g) detecting the presence or absence of the label on the solid support.

2. The method of claim 1, wherein the one or more nucleic acids of interest comprise five or more, 10 or more, 20 or more, 30 or more, 40 or more, or 50 or more different nucleic acids of interest, which different nucleic acids of interest are different nucleic acid molecules; and wherein the one or more subsets of m label extenders comprise five, or more, 10 or more, 20 or more, 30 or more, 40 or more, or 50 or more different subsets of m label extenders.

3. The method of claim 1, wherein the label probe system comprises a preamplifier, an amplification multimer and a label probe; wherein the preamplifier is capable of hybridizing simultaneously to the at least two of the m label extenders and to a plurality of amplification multimers; wherein the amplification multimer is capable of hybridizing simultaneously to the preamplifier and to a plurality of label probes; and wherein the label probe comprises the label.

4. The method of claim 1, comprising separating materials not captured on the solid support from the solid support.

5. The method of claim 1, wherein the one or more nucleic acids of interest are derived from one or more of: an animal, a human, a plant, a cultured cell, a microorganism, a virus, a bacterium, or a pathogen.

6. The method of claim 1, wherein the sample comprises one or more of: a cell lysate, an intercellular fluid, a bodily fluid, or a conditioned culture medium.

7. The method of claim 1, wherein the sample is derived from one or more of: a tissue, a biopsy, or a tumor.

8. The method of claim 1, wherein the one or more nucleic acids of interest comprise two or more nucleic acids of interest, and wherein the two or more nucleic acids of interest comprise two or more mRNAs.

9. The method of claim 1, wherein the one or more nucleic acids of interest comprise two or more different nucleic acids of interest, which different nucleic acids of interest are different nucleic acid molecules, and wherein the one or more subsets of m label extenders comprise two or more different subsets of m label extenders.

10. The method of claim 9, wherein capturing the nucleic acids of interest present in the sample on the solid support comprises:
providing a pooled population of particles which constitute the solid support, the population comprising two or more subsets of particles, a plurality of the particles in each subset being distinguishable from a plurality of the particles in every other subset, and the particles in each subset having associated therewith a different capture probe;
providing two or more subsets of n capture extenders, wherein n is at least two, wherein each subset of n capture extenders is capable of hybridizing to one of the nucleic acids of interest, and wherein the capture extenders in each subset are capable of hybridizing to one of the capture probes and thereby associating each subset of n capture extenders with a selected subset of the particles; and
hybridizing each of the nucleic acids of interest present in the sample to its corresponding subset of n capture extenders and hybridizing the subset of n capture extenders to its corresponding capture probe, whereby the hybridizing the nucleic acid of interest to the n capture extenders and the n capture extenders to the corresponding capture probe captures the nucleic acid on the subset of particles with which the capture extenders are associated.

11. The method of claim 10, wherein detecting the presence or absence of the label on the solid support comprises identifying at least a portion of the particles from each subset and detecting the presence or absence of the label on those particles, thereby determining which subsets of particles have a nucleic acid of interest captured on the particles and indicating which of the nucleic acids at interest were present in the sample.

12. The method of claim 9, wherein the solid support is spatially addressable and comprises two or more different capture probes, wherein each different capture probe is provided at a different selected position on the solid support; and wherein capturing the nucleic acids of interest present in the sample on the solid support comprises:
providing two or more subsets of n capture extenders, wherein n is at least two, wherein each subset of n capture extenders is capable of hybridizing to a different one at the nucleic acids of interest, and wherein the capture extenders in each subset are capable of hybridizing to one of the capture probes and thereby associating each subset of n capture extenders with a selected position on the solid support; and
hybridizing each of the nucleic acids of interest present in the sample to its corresponding subset of n capture extenders and hybridizing the subset of n capture extenders to its corresponding capture probe, whereby the hybridizing the nucleic acid of interest to the n capture extenders and the n capture extenders to the corresponding capture probe captures the nucleic acid on the solid support at the selected position with which the capture extenders are associated.

13. The method of claim 12, wherein detecting the presence or absence of the label on the solid support comprises detecting the presence or absence of the label at the selected positions on the solid support, thereby determining which selected positions have a nucleic acid of interest captured at that position and indicating which of the nucleic acids of interest were present in the sample.

14. The method of claim 1, wherein the label is a fluorescent label, and wherein detecting the presence of the label comprises detecting a fluorescent signal from the label.

15. The method of claim 1, wherein detecting the presence of the label on the solid support comprises measuring an intensity on signal from the label, the method comprising correlating the intensity of the signal with a quantity of the nucleic acids or interest present.

16. The method of claim 1, wherein the label probe system comprises an amplification multimer or preamplifier, which amplification multimer or preamplifier is capable of hybridizing to the at least two label extenders.

17. The method of claim 1, wherein the hybridization temperature is about 5° C. or more greater than the $T_m$ of a complex between each individual label extender and the component of the label probe system.

18. The method of claim 17, wherein the hybridization temperature is about 7° C. or more, about 10° C. or more, about 12° C. or more, about 15° C. or more, about 17° C. or more, or about 20° C. or more greater than the $T_m$ of a complex between each individual label extender and the component of the label probe system.

19. The method of claim 1, wherein polynucleotide sequence L-2 is 20 nucleotides or less in length.

20. The method of claim 19, wherein L-2 is between 9 and 17 nucleotides in length.

21. The method of claim 20, wherein L-2 is between 13 and 15 nucleotides in length.

22. The method of claim 1, wherein each of said at least two label extenders has L-1 at its 5' end and L-2 at its 3' end.

23. The method of claim 1, wherein each of said at least two label extenders has L-1 at its 3' end and L-2 at its 5' end.

24. The method of claim 1, wherein the in label extenders in a subset all have L-1 5' of L-2 or all have L-1 3' of L-2.

25. The method of claim 1, wherein the label probe system comprises an amplification multimer and a label probe; wherein the amplification multimer is capable of hybridizing simultaneously to the at least two of the m label extenders and to a plurality of label probes; and wherein the label probe comprises the label.

26. The method of claim 1, wherein the label probe system comprises a label probe; wherein the label probe is capable of hybridizing simultaneously to the at least two of the m label extenders; and wherein the label probe comprises the label.

27. The method of claim 1, wherein the component of the label probe system is capable of hybridizing simultaneously to two of the m label extenders in a subset.

28. A method of capturing a label to a nucleic acid of interest, the method comprising:
 a) providing m label extenders, wherein m is at least two, wherein the m label extenders are capable of hybridizing to nonoverlapping sequences in the nucleic acid of interest;
 b) providing a label probe system comprising the label, wherein a component of the label probe system is capable of hybridizing simultaneously to at least two of the m label extenders, wherein each of said at least two label extenders comprises a polynucleotide sequence L-1 that is complementary to a polynucleotide sequence in the nucleic acid of interest and comprises a polynucleotide sequence L-2 that is complementary to a polynucleotide sequence in the component of the label probe system, and wherein said at least two label extenders all have L-1 5' of L-2 or all have L-1 3' of L-2;
 c) hybridizing the nucleic acid of interest to the m label extenders; and
 d) hybridizing the label probe system to the m label extenders at a hybridization temperature, which hybridization temperature is greater than a melting temperature $T_m$ of a complex between each individual label extender and the component of the label probe system, thereby capturing the label to the nucleic acid of interest.

29. The method of claim 28, wherein the m label extenders all have L-1 5' of L-2 or all have L-1 3' of L-2.

30. The method of claim 28, wherein the label probe system comprises an amplification multimer or preamplifier, which amplification multimer or preamplifier is capable of hybridizing to the at least two of the m label extenders.

31. The method of claim 28, wherein the label probe system comprises a preamplifier, an amplification multimer and a label probe; wherein the preamplifier is capable of hybridizing simultaneously to the at least two of the m label extenders and to a plurality of amplification multimers; wherein the amplification multimer is capable of hybridizing simultaneously to the preamplifier and to a plurality of label probes; and wherein the label probe comprises the label.

32. The method of claim 28, wherein the label probe system comprises an amplification multimer and a label probe; wherein the amplification multimer is capable of hybridizing simultaneously to the at least two of the m label extenders and to a plurality of label probes; and wherein the label probe comprises the label.

33. The method of claim 28, wherein the label probe system comprises a label probe; wherein the label probe is capable of hybridizing simultaneously to the at least two of the m label extenders; and wherein the label probe comprises the label.

34. The method of claim 28, wherein the component of the label probe system is capable of hybridizing simultaneously to two of the m label extenders.

35. The method of claim 28, wherein the hybridization temperature is about 5° C. or more greater than the $T_m$ of a complex between each individual label extender and the component of the label probe system.

36. The method of claim 28, wherein the hybridization temperature is about 7° C. or more, about 10° C. or more, about 12° C. or more, about 15° C. or more, about 17° C. or more, or about 20° C. or more greater than the $T_m$ of a complex between each individual label extender and the component of the label probe system.

37. The method of claim 28, wherein polynucleotide sequence L-2 is 20 nucleotides or less in length.

38. The method of claim 37, wherein L-2 is between 9 and 17 nucleotides in length.

39. The method of claim 38, wherein L-2 is between 13 and 15 nucleotides in length.

40. The method of claim 28, wherein each of said at least two label extenders has L-1 at its 5' end and L-2 at its 3' end.

41. The method of claim 28, wherein each of said at least two label extenders has L-1 at its 3' end and L-2 at its 5' end.

42. The method of claim 28, comprising capturing the nucleic acid of interest on a solid support.

43. The method of claim 28, comprising detecting a signal from the label.

44. A method of detecting one or more nucleic acids of interest, the method comprising:
 a) providing a sample comprising the one or more nucleic acids of interest;
 b) capturing the nucleic acids of interest on a solid support;
 c) providing a label probe system comprising a label;
 d) for each of the nucleic acids of interest, providing a subset of m label extenders, wherein m is at least two, wherein the subset of m label extenders is capable of hybridizing to that nucleic acid of interest, wherein a component of the label probe system is capable of hybridizing simultaneously to at least two of the m label extenders in the subset, wherein each of said at least two label extenders comprises a polynucleotide sequence L-1 that is complementary to a polynucleotide sequence in the nucleic acid of interest and comprises a polynucleotide sequence L-2 that is complementary to a polynucleotide sequence in the component of the label probe system, and wherein said at least two label extenders all have L-1 5' of L-2 or all have L-1 3' of L-2;
 e) hybridizing each nucleic acid of interest to its corresponding subset of m label extenders;
 f) hybridizing the label probe system to the label extenders at a hybridization temperature, which hybridization temperature is greater than a melting temperature $T_m$ of a complex between each individual label extender and the component of the label probe system, whereby, for each of the nucleic acids of interest, a single copy of each of said at least two label extenders hybridizes simultaneously to a single copy of the nucleic acid of interest and to a single copy of the component of the label probe system; and
 g) detecting the presence or absence of the label on the solid support.

45. A method of capturing a label to a nucleic acid of interest, the method comprising:
 a) providing m label extenders, wherein m is at least two, wherein the m label extenders are capable of hybridizing to the nucleic acid of interest;
 b) providing a label probe system comprising the label, wherein a component of the label probe system is capable of hybridizing simultaneously to at least two of the m label extenders, wherein each of said at least two label extenders comprises a polynucleotide sequence L-1 that is complementary to a polynucleotide sequence in the nucleic acid of interest and comprises a polynucleotide sequence L-2 that is complementary to a polynucleotide sequence in the component of the label probe system, and wherein said at least two label extenders all have L-1 5' of L-2 or all have L-1 3' of L-2;
 c) hybridizing the nucleic acid of interest to the m label extenders; and d) hybridizing the label probe system to the m label extenders at a hybridization temperature, which hybridization temperature is greater than a melting temperature $T_m$ of a complex between each individual label extender and the component of the label probe system, whereby a single copy of each of said at least two label extenders hybridizes simultaneously to a single copy of the nucleic acid of interest and to a single copy of the component of the label probe system, thereby capturing the label to the nucleic acid of interest.

* * * * *

UNITED STATES PATENT AND TRADEMARK OFFICE
CERTIFICATE OF CORRECTION

| | | |
|---|---|---|
| PATENT NO. | : 7,709,198 B2 | Page 1 of 1 |
| APPLICATION NO. | : 11/471025 | |
| DATED | : May 4, 2010 | |
| INVENTOR(S) | : Yuling Luo et al. | |

It is certified that error appears in the above-identified patent and that said Letters Patent is hereby corrected as shown below:

Title page item (73), Assignee address "Haywood, CA" should be --Hayward, CA--.

In claim 11, at column 43, line 57, "nucleic acids at interest" should be --nucleic acids of interest--.

In claim 12, at column 44, line 1, "at the nucleic acids of interest" should be --of the nucleic acids of interest--.

In claim 15, at column 44, line 27, "intensity on signal" should be --intensity of signal--.

In claim 15, at column 44, line 29, "nucleic acids or interest" should be --nucleic acids of interest--.

In claims 17 and 18, all occurrences of "C." should be --C--.

In claim 24, at column 44, line 56, "in label extenders" should be --m label extenders--.

In claim 28, at column 45, line 6, "wherein in is" should be --wherein m is--.

In claim 28, at column 45, lines 23-24, "in label extenders" should be --m label extenders--.

In claim 29, at column 45, line 29, "in label extenders" should be --m label extenders--.

Signed and Sealed this

Twenty-ninth Day of June, 2010

David J. Kappos
*Director of the United States Patent and Trademark Office*

SEQUENCE LISTING

```
<160> NUMBER OF SEQ ID NOS: 13

<210> SEQ ID NO 1
<211> LENGTH: 81
<212> TYPE: DNA
<213> ORGANISM: Artificial
<220> FEATURE:
<223> OTHER INFORMATION: synthetic oligonucleotide probe

<400> SEQUENCE: 1
aggcatagga cccgtgtctt ttttttttta ggcataggac ccgtgtcttt tttatgcttt     60
gactcagaaa acggtaactt c                                              81

<210> SEQ ID NO 2
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 2
ccagtggact ccacgacgta cttttgaag ttaccgtttt                            40

<210> SEQ ID NO 3
<211> LENGTH: 40
<212> TYPE: DNA
<213> ORGANISM: Artificial
<220> FEATURE:
```

<223> OTHER INFORMATION: synthetic oligonucleotide probe

<400> SEQUENCE: 3
ctgagtcaaa gcatttttt tctccatggt ggtgaagacg                    40

<210> SEQ ID NO 4
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 4
tcttgaggct gttgtcatac ttcttttttg aagttaccgt ttt               43

<210> SEQ ID NO 5
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 5
ctgagtcaaa gcattttttg caggaggcat tgctgatga                    39

<210> SEQ ID NO 6
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 6
cagtagaggc agggatgatg ttcttttttga agttaccgtt tt               42

<210> SEQ ID NO 7
<211> LENGTH: 36
<212> TYPE: DNA
<213> ORGANISM: Artificial
<220> FEATURE:
<223> OTHER INFORMATION: synthetic oligonucleotide probe

<400> SEQUENCE: 7
ctgagtcaaa gcatttttc acagccttgg cagcgc                        36

<210> SEQ ID NO 8
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 8
ccagtggact ccacgacgta cttttttgaag ttaccgtttt                  40

<210> SEQ ID NO 9
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 9
ttctccatgg tggtgaagac gttttttctga gtcaaagcat                  40

-continued

```
<210> SEQ ID NO 10
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 10
tcttgaggct gttgtcatac ttcttttttg aagttaccgt ttt                    43

<210> SEQ ID NO 11
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 11
gcaggaggca ttgctgatga tttttctgag tcaaagcat                         39

<210> SEQ ID NO 12
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 12
cagtagaggc agggatgatg ttcttttga agttaccgtt tt                      42

<210> SEQ ID NO 13
<211> LENGTH: 36
<212> TYPE: DNA
<213> ORGANISM: Artificial
<220> FEATURE:
<223> OTHER INFORMATION: synthetic oligonucleotide probe

<400> SEQUENCE: 13
cacagccttg gcagcgcttt ttctgagtca aagcat                            36
```